(12) United States Patent
Rapacki et al.

(10) Patent No.: US 6,651,670 B2
(45) Date of Patent: *Nov. 25, 2003

(54) DELIVERING A CONDUIT INTO A HEART WALL TO PLACE A CORONARY VESSEL IN COMMUNICATION WITH A HEART CHAMBER AND REMOVING TISSUE FROM THE VESSEL OR HEART WALL TO FACILITATE SUCH COMMUNICATION

(75) Inventors: Alan R. Rapacki, Redwood City, CA (US); Darin C. Gittings, Sunnyvale, CA (US); Gilbert S. Laroya, Menlo Park, CA (US); Mark J. Foley, Menlo Park, CA (US)

(73) Assignee: Ventrica, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/170,994

(22) Filed: Oct. 13, 1998

(65) Prior Publication Data

US 2002/0161424 A1 Oct. 31, 2002

Related U.S. Application Data

(63) Continuation-in-part of application No. 09/023,492, filed on Feb. 13, 1998, now abandoned.

(51) Int. Cl.$^7$ .............................................. A61B 17/00
(52) U.S. Cl. ................................................... 128/898
(58) Field of Search ............................ 128/898; 606/108

(56) References Cited

U.S. PATENT DOCUMENTS

| | | | | | |
|---|---|---|---|---|---|
| 5,429,144 | A | * | 7/1995 | Wilk | 128/898 |
| 5,908,029 | A | * | 6/1999 | Knodson et al. | 128/898 |
| 5,944,019 | A | * | 8/1999 | Knudson et al. | 128/898 |
| 6,080,163 | A | * | 6/2000 | Hussein et al. | 606/108 |
| 6,092,526 | A | * | 7/2000 | LaFontaine et al. | 128/898 |
| 6,139,541 | A | * | 10/2000 | Vanney et al. | 606/108 |
| 6,196,230 | B1 | * | 3/2001 | Hall et al. | 606/108 |

* cited by examiner

*Primary Examiner*—Cary E. O'Connor
(74) *Attorney, Agent, or Firm*—Hoekendijk & Lynch, LLP

(57) ABSTRACT

Devices and methods for delivering conduits into the wall of a patient's heart to communicate a coronary vessel with a heart chamber. The devices are passed through the coronary vessel and the heart wall to place the conduit and establish a blood flow path between the vessel and the heart chamber. Additional devices and methods are provided for removing tissue from a coronary vessel or the heart wall to establish a flow path between the coronary vessel in communication with the heart chamber.

16 Claims, 20 Drawing Sheets

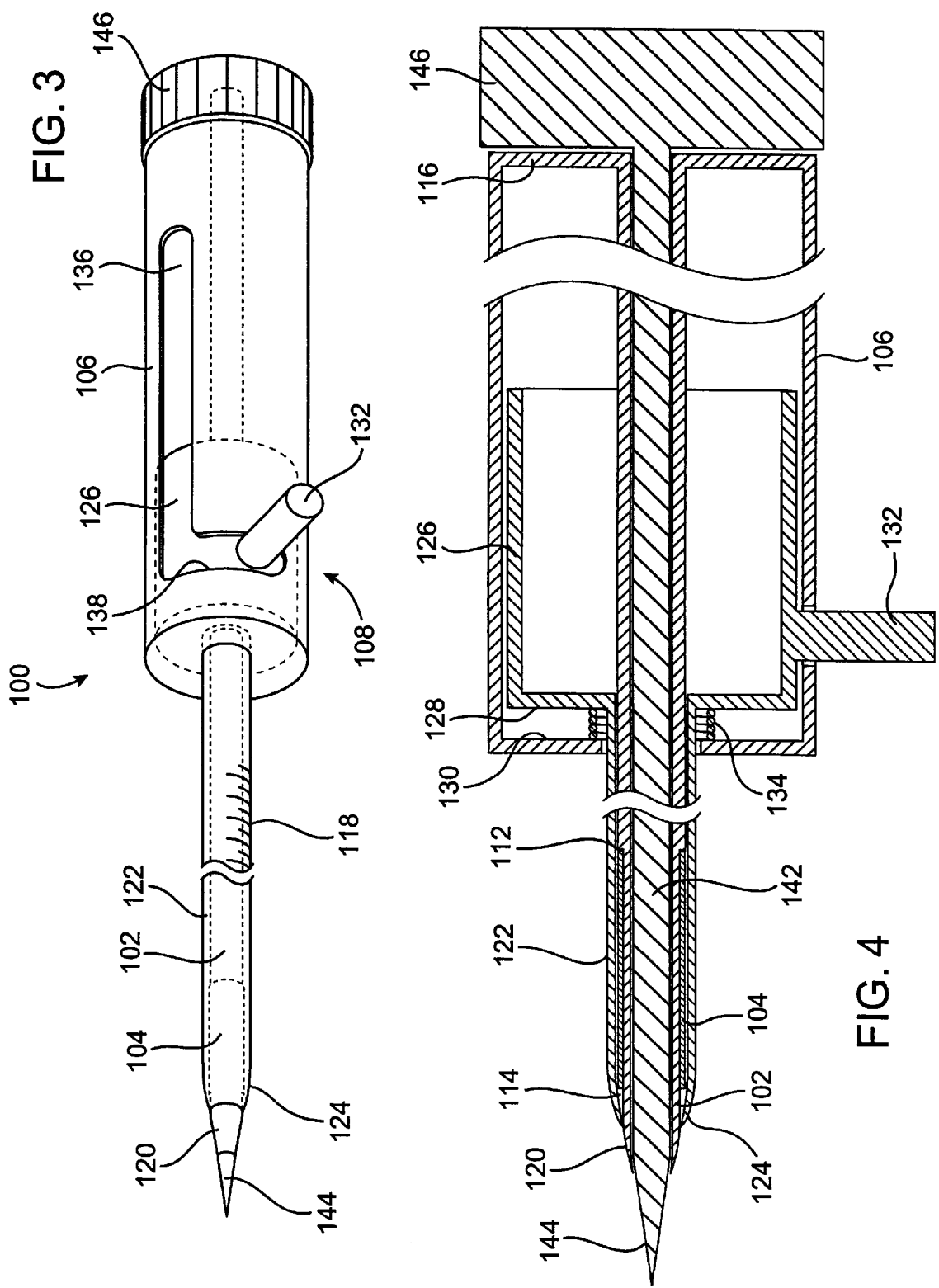

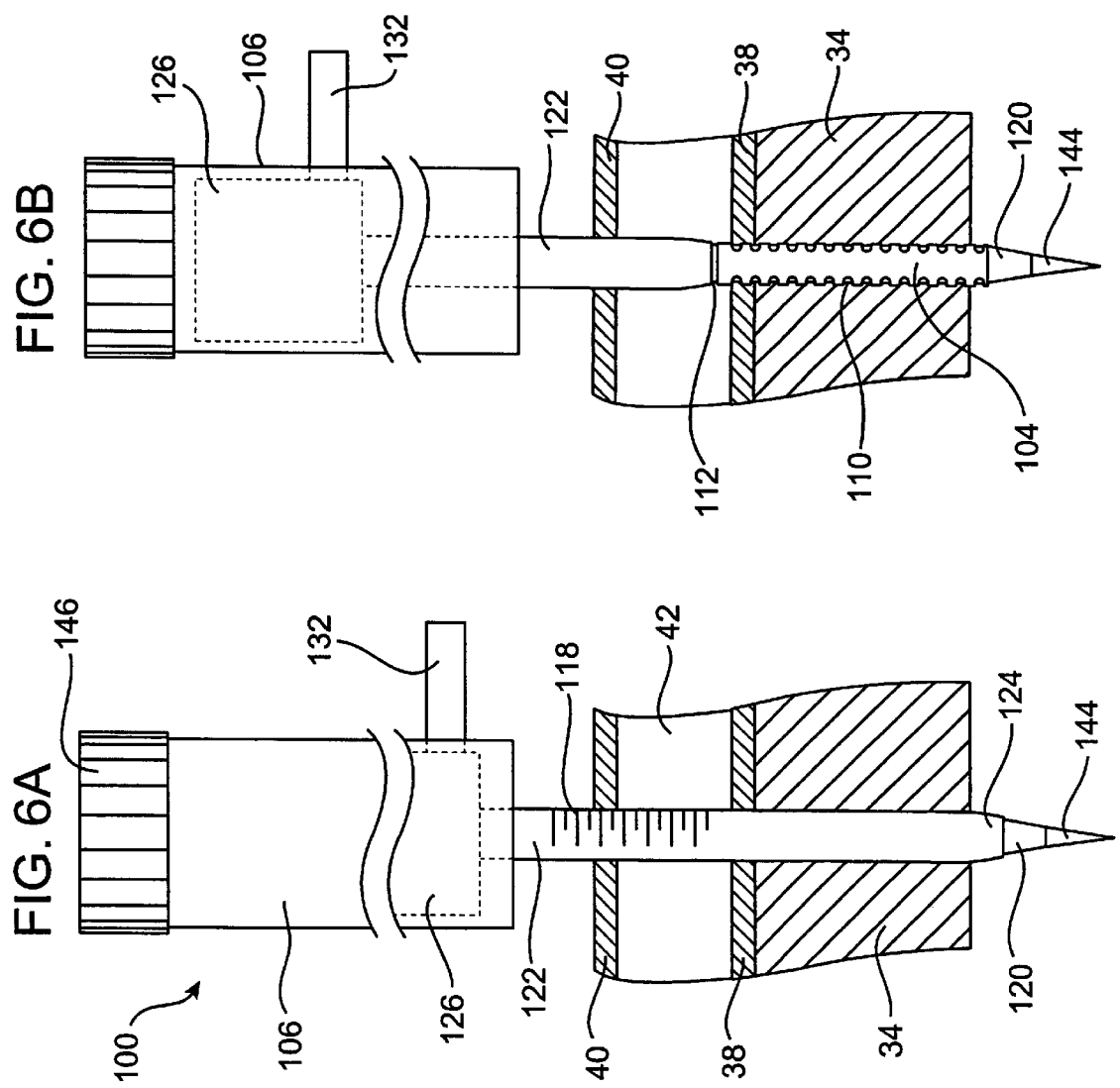

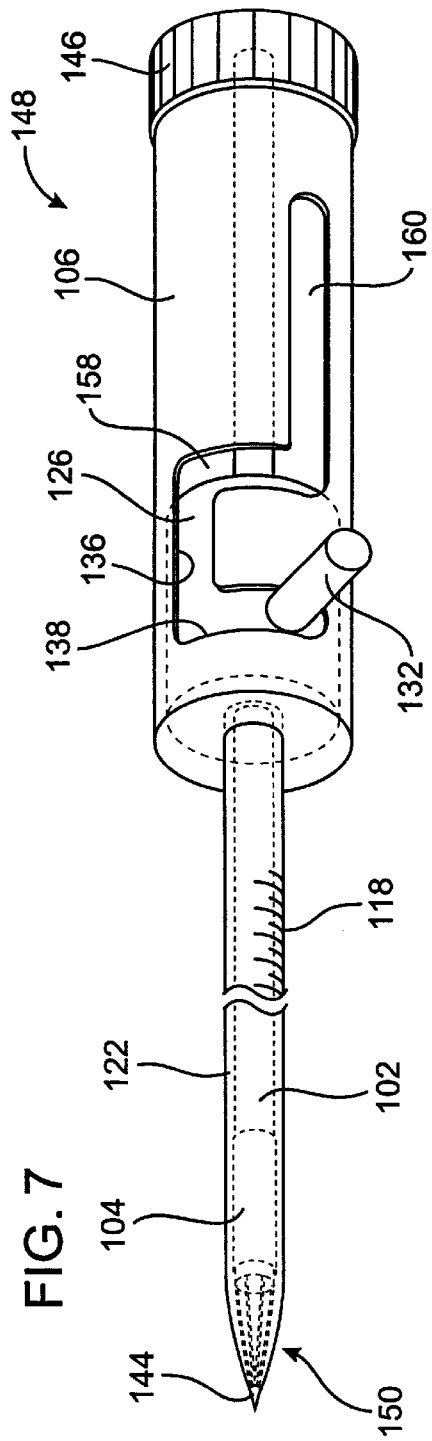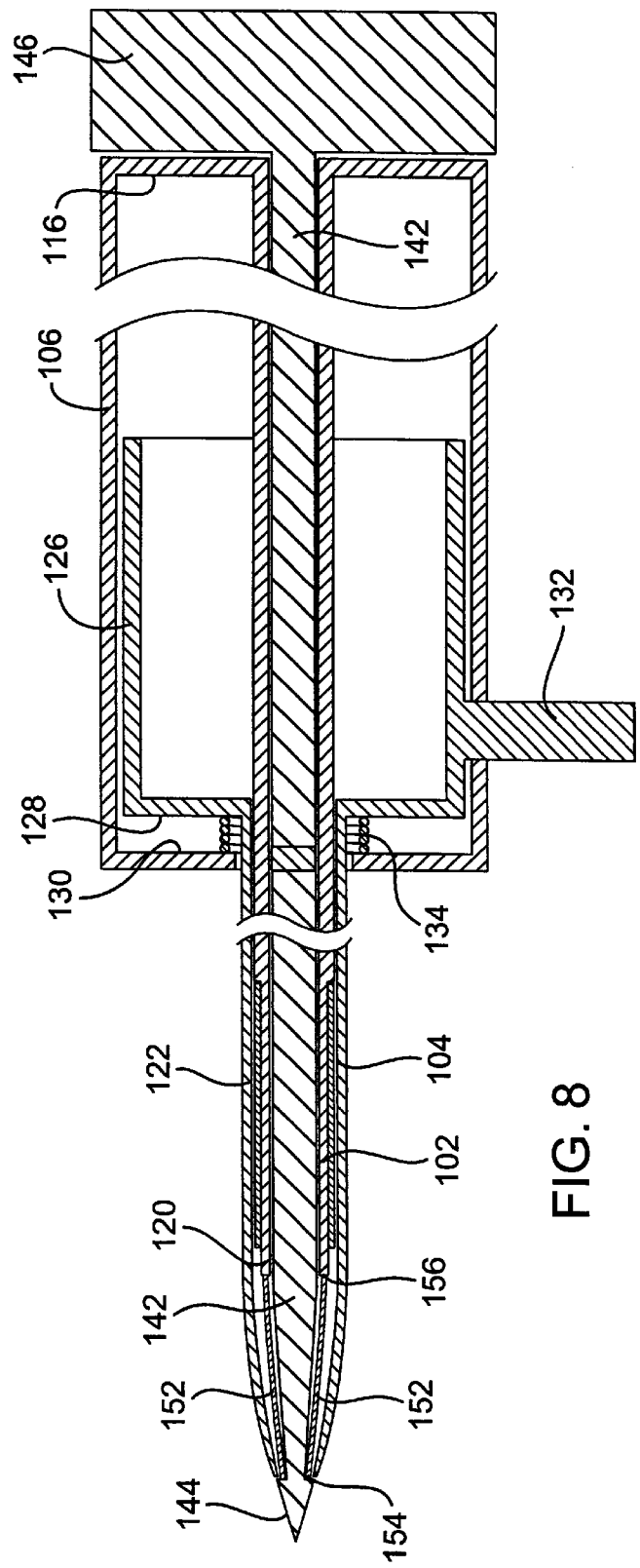

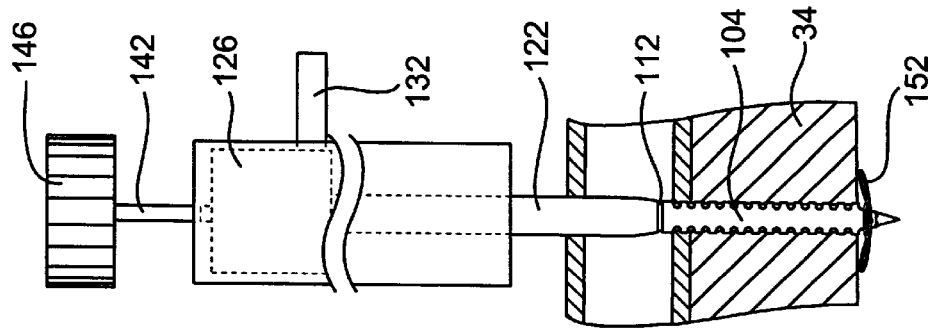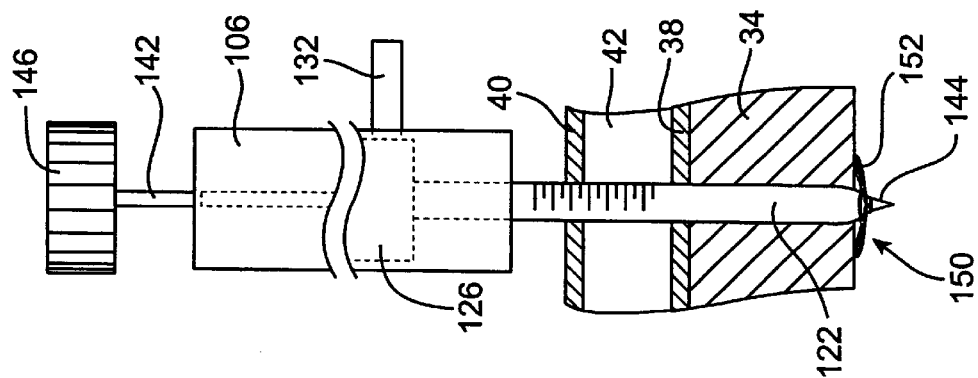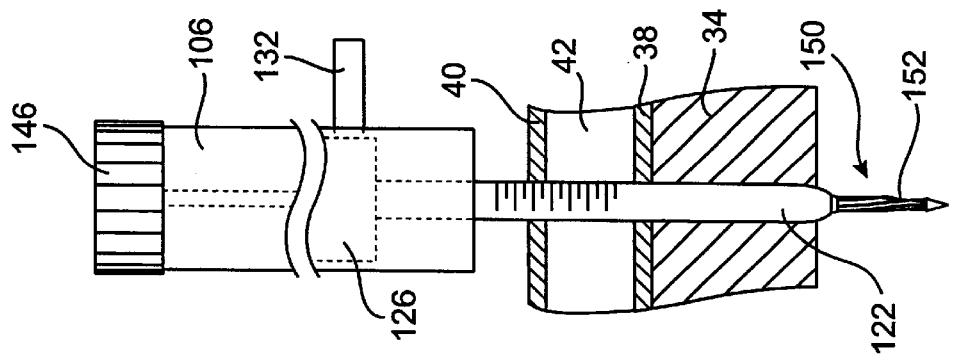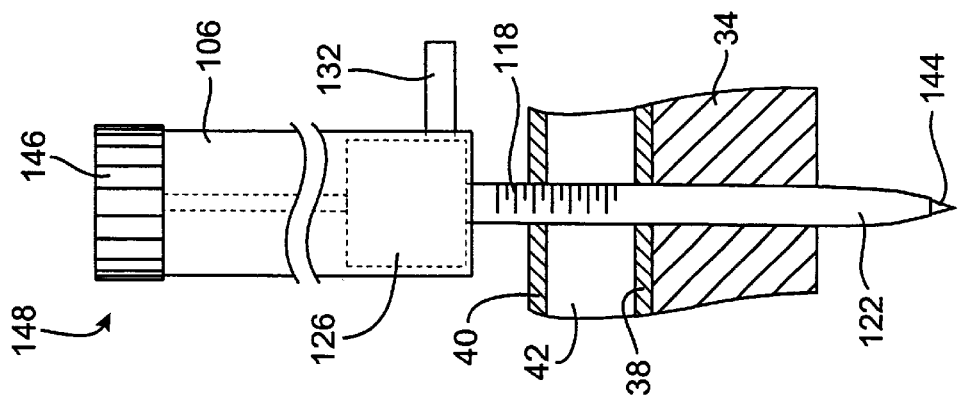

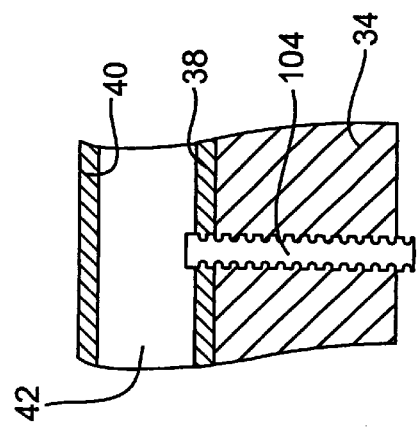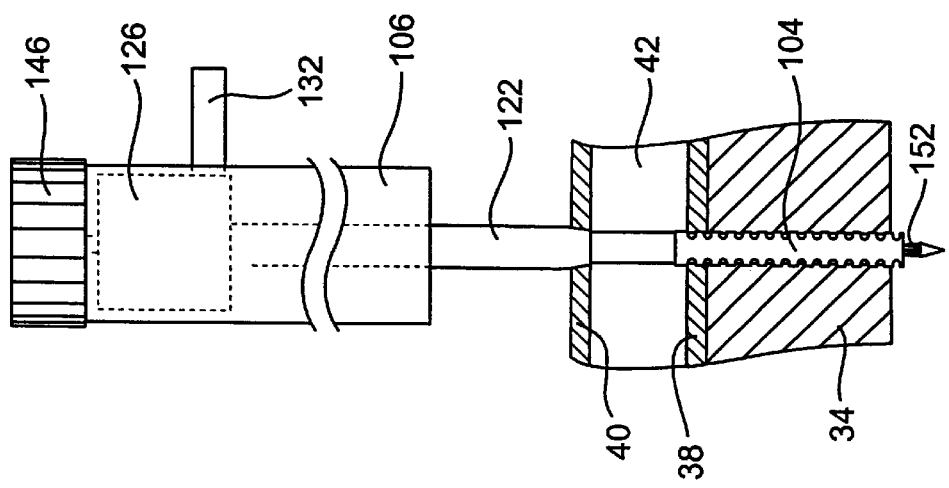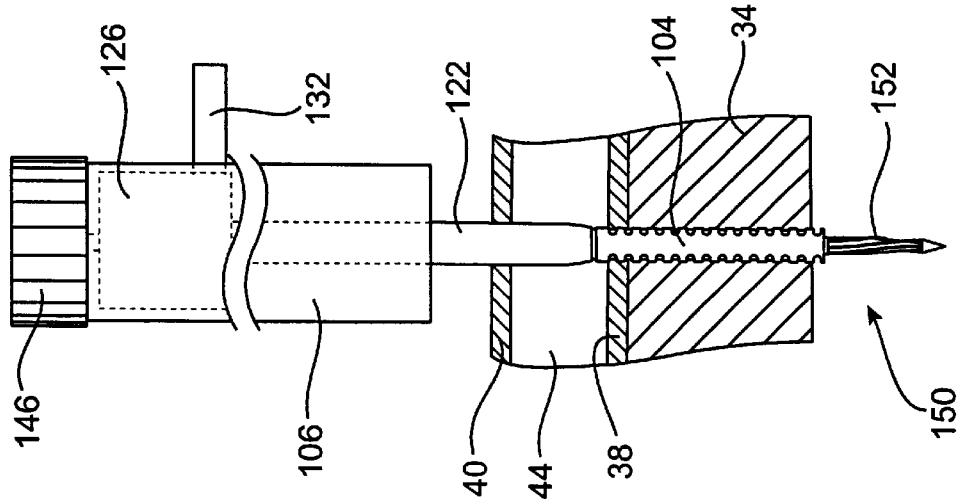

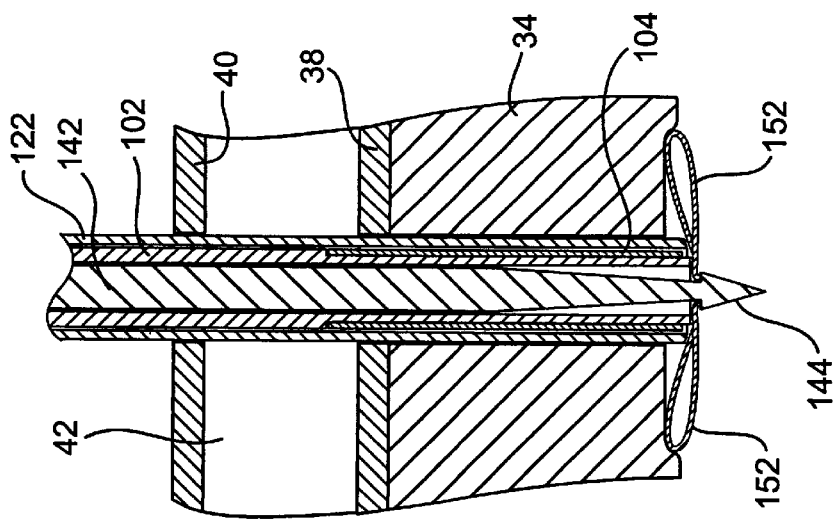
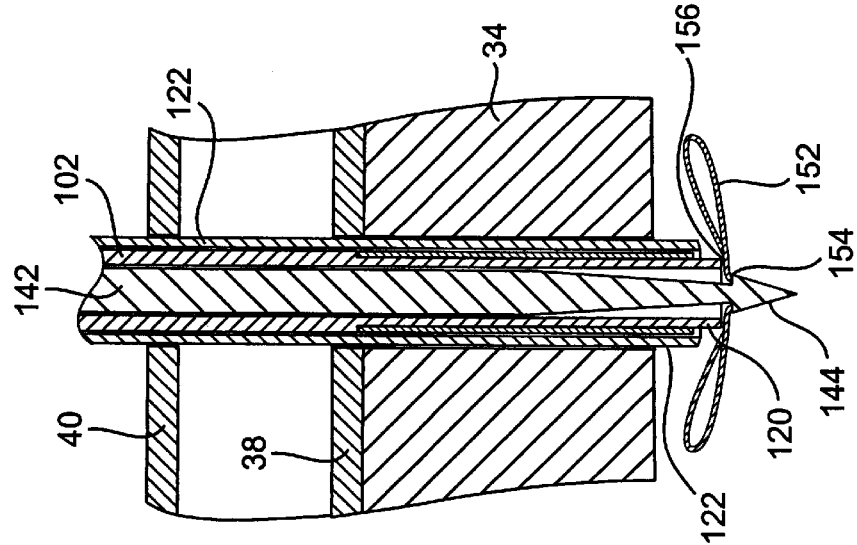
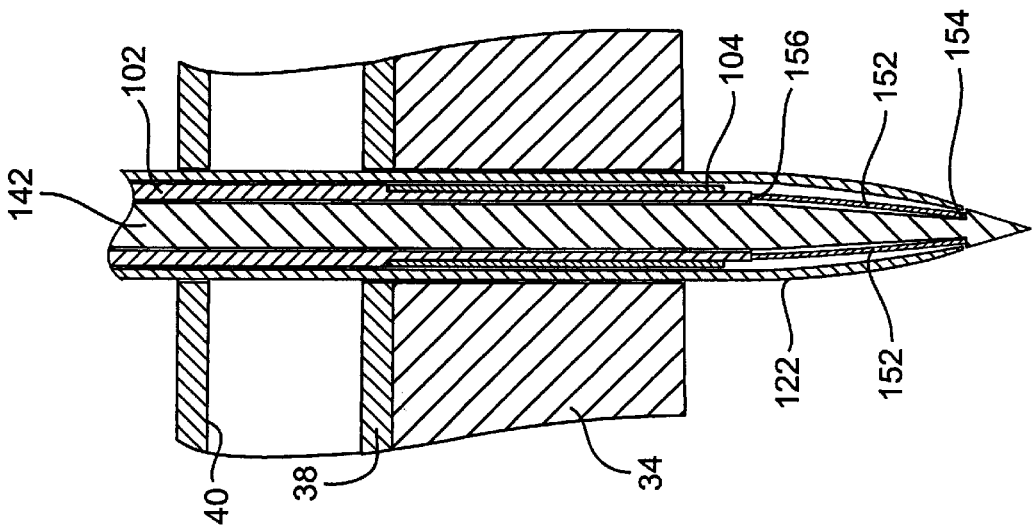

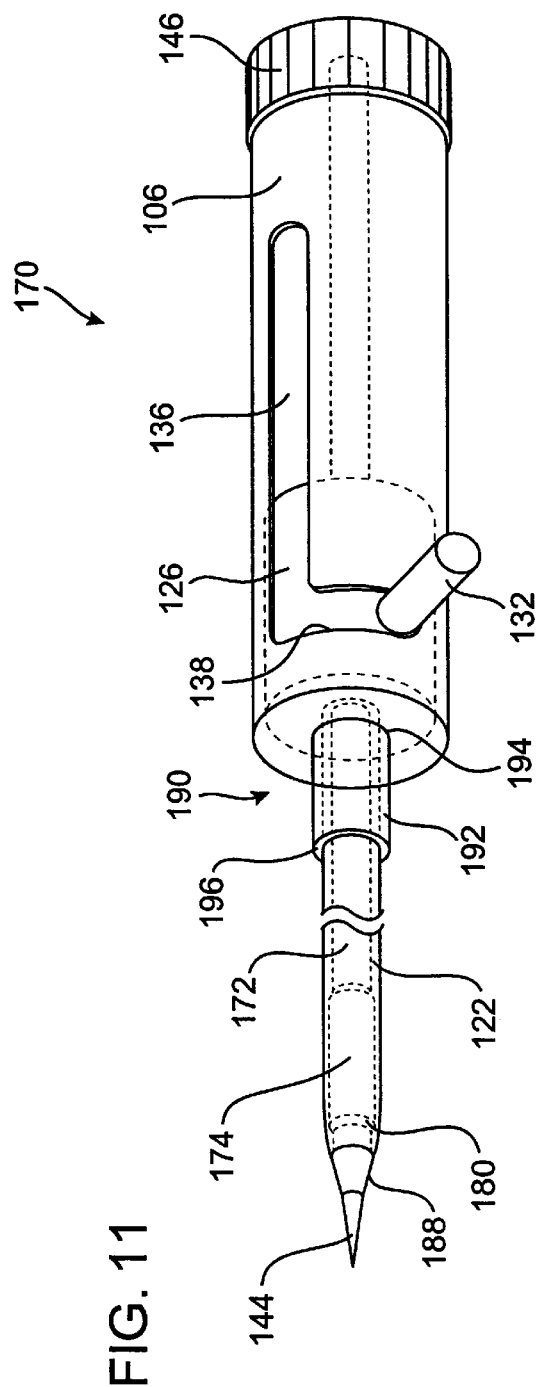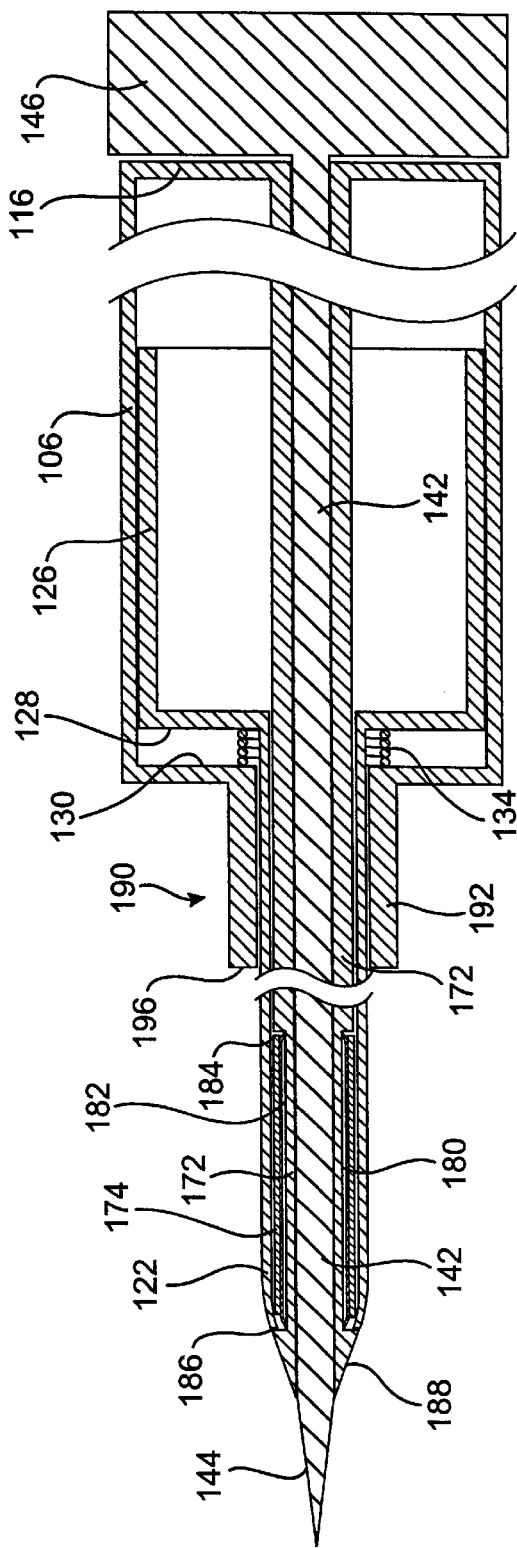

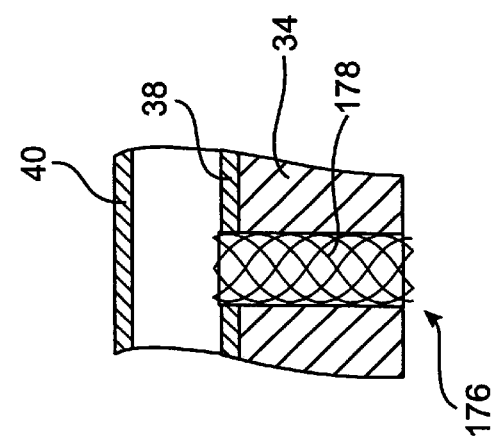
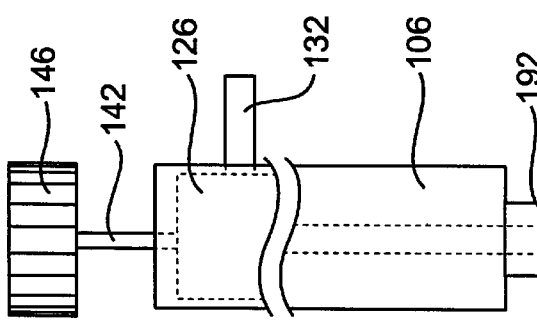
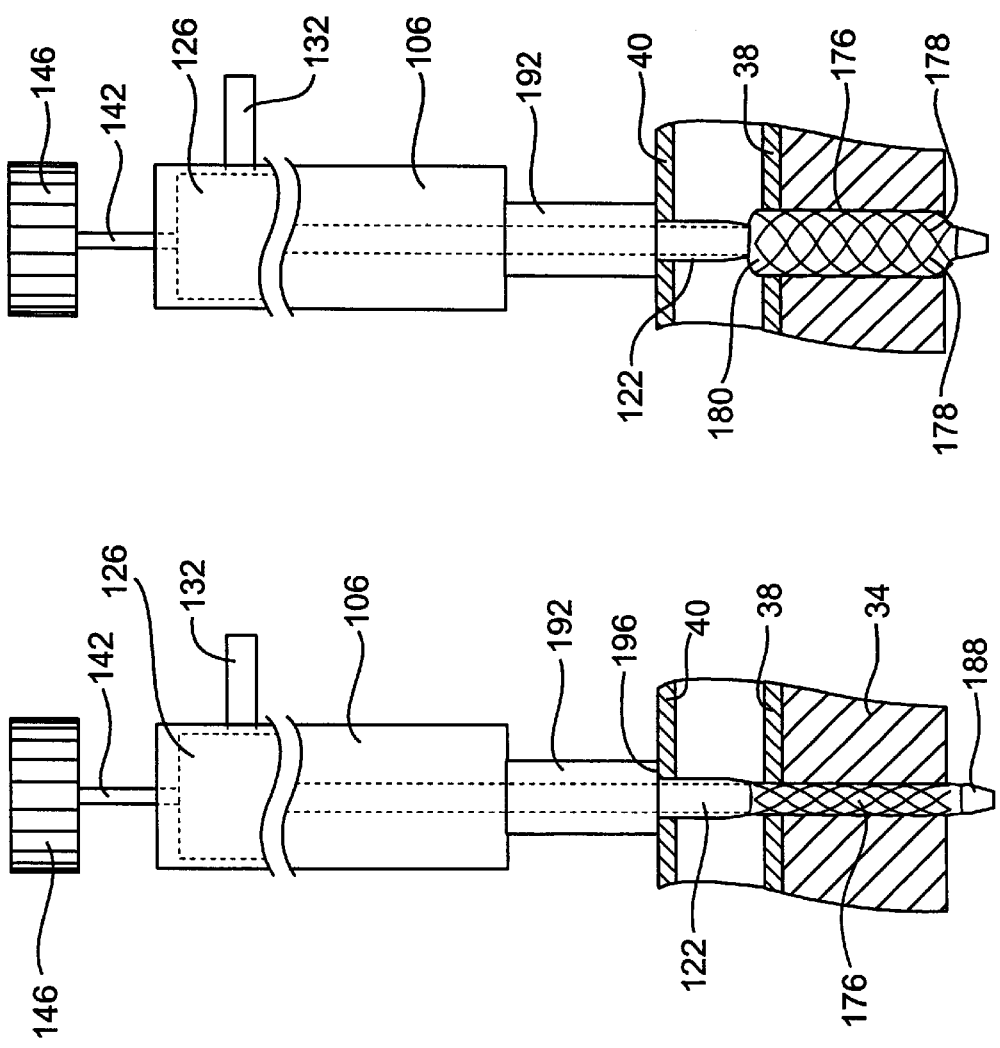

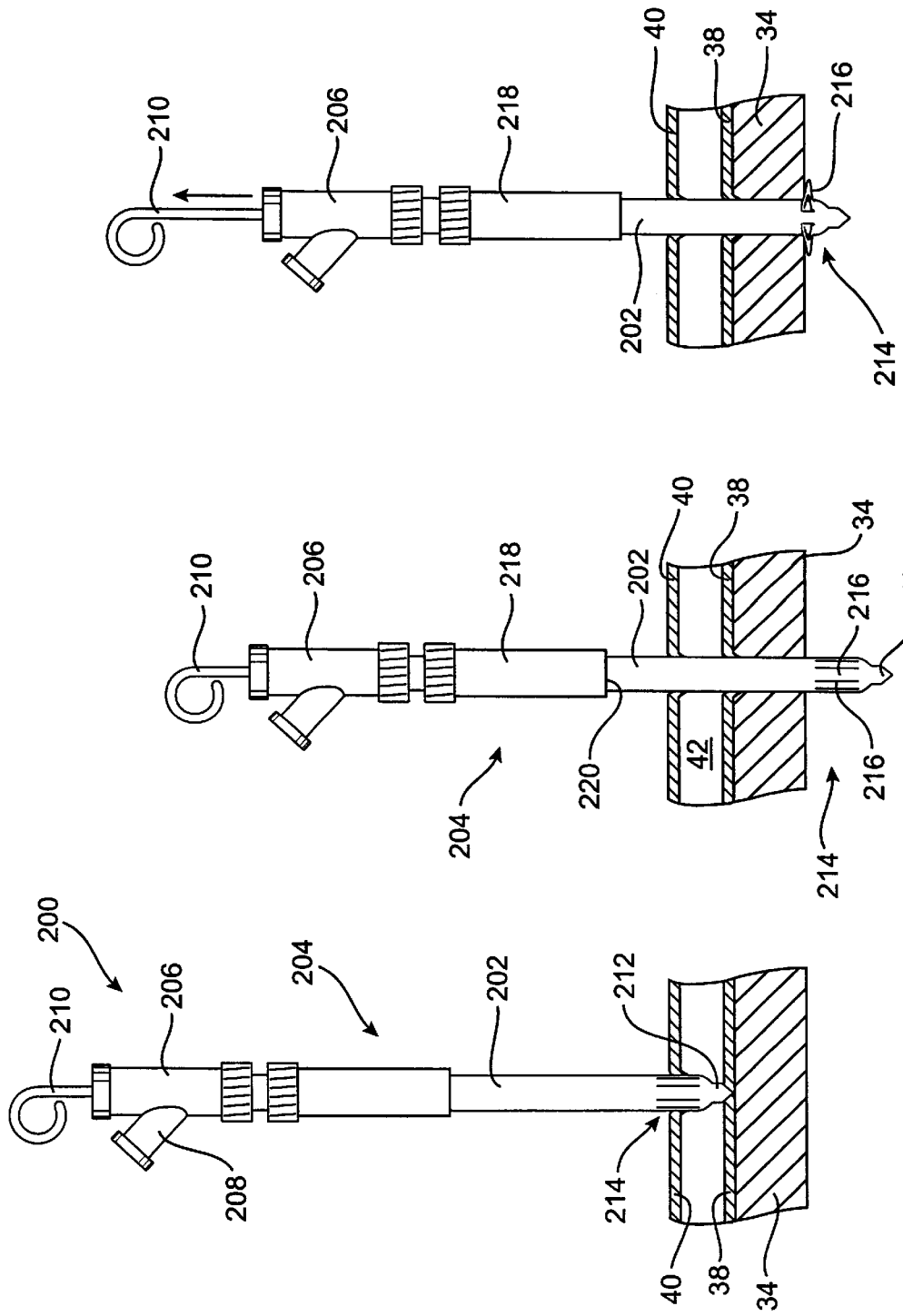

DELIVERING A CONDUIT INTO A HEART WALL TO PLACE A CORONARY VESSEL IN COMMUNICATION WITH A HEART CHAMBER AND REMOVING TISSUE FROM THE VESSEL OR HEART WALL TO FACILITATE SUCH COMMUNICATION

CROSS-REFERENCE TO RELATED APPLICATIONS

This application is a continuation-in-part of application Ser. No. 09/023,492, filed Feb. 13, 1998 now abandoned, and entitled "Methods and Devices Providing Transmyocardial Blood Flow to the Arterial Vascular System of the Heart," the entire subject matter of which application is incorporated herein by reference.

BACKGROUND OF THE INVENTION

1. Field of the Invention

The invention relates to treating heart disease, and more particularly systems, devices and methods for reestablishing or improving blood flow to the myocardium.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue the search for new and improved treatments.

Coronary artery disease is currently treated by interventional procedures such as percutaneous transluminal coronary angioplasty (PTCA), atherectomy and coronary stenting, as well as surgical procedures including coronary artery bypass grafting (CABG). The goal of these procedures is to reestablish or improve blood flow through occluded (or partially occluded) coronary arteries, which is accomplished, for example, by enlarging the blood flow lumen of the artery or by forming a bypass that allows blood to circumvent the occlusion. What procedure(s) is used typically depends on the severity and location of the blockages. When successful, these procedures restore blood flow to myocardial tissue that had not been sufficiently perfused due to the occlusion.

Technological and procedural advances have improved the results obtained by the medical procedures now used to treat heart disease, and in particular coronary artery disease. There is, however, still much room for improvement. For that reason there remains a need in the art for new and improved systems, devices and methods for treating heart disease such as arteriosclerosis.

SUMMARY OF THE INVENTION

In one embodiment, the invention provides a device for delivering a conduit into the wall of a patient's heart to place the conduit in communication with a heart chamber. The device includes a support member, a conduit disposed on the support member, and a sheath overlying at least a portion of the conduit. The sheath is moved to expose a portion of the conduit upon positioning the support member and conduit at a desired location within the wall of the heart.

In another embodiment, the invention provides a device for delivering a conduit to a selected location in the wall of a patient's heart to place the conduit in communication with a heart chamber. The device includes a support member, a conduit disposed on the support member, and a positioning member configured to engage tissue so as to place the conduit in a selected position within the heart wall. The positioning member is disposed a predetermined distance from the conduit. The position of the conduit relative to the heart wall is determined by the location of the positioning member relative to the heart wall.

In another embodiment, the invention provides a device for delivering a conduit through the wall of a patient's heart and the wall of a coronary vessel to communicate a heart chamber with the coronary vessel. The device includes a support member configured for placement through the wall of a heart into a heart chamber, and an expandable conduit sized and configured for placement in the heart wall so as to communicate the heart chamber with a coronary vessel. The conduit is supported on the support member in a collapsed orientation and moved to an expanded orientation by an expansion mechanism on the support member.

In yet another embodiment, the invention provides a method for placing a conduit in the wall of a patient's heart. The method includes providing a support member and a conduit, passing the support member and the conduit through a wall of a coronary vessel and through the wall of a patient's heart, positioning the conduit within the wall of the heart, and removing the support member and leaving the conduit in the wall of the heart.

In another embodiment, the invention provides a method for placing a conduit in the wall of a patient's heart at a selected position with respect to the heart wall. The method includes providing a support member and a conduit, the support member having a positioning member disposed at a predetermined location with respect to the conduit. The support member and conduit are passed through a wall of a coronary vessel and through the wall of a patient's heart, and the positioning member is located against tissue to place the conduit at a selected location within the wall of the heart. The support member is removed leaving the conduit in the wall of the heart.

In still another embodiment, the invention provides a method for placing and expanding a conduit in the wall of a patient's heart. The method includes providing a support member and a conduit, the conduit being supported in a collapsed orientation and movable to an expanded orientation. The support member and the conduit are placed in the wall of a patient's heart, the conduit is expanded and the support member is removed while leaving the conduit in the wall of the heart.

In yet another embodiment, the invention provides a device and method for forming a channel that extends at least partially through the wall of a patient's heart and communicates with a heart chamber. This embodiment includes a shaft and a tissue removal mechanism movably supported on the shaft. The tissue removal mechanism including a tissue-removing portion that is actuated to remove a section of tissue from a patient's heart to form a channel that extends at least partially through the heart wall and communicates with a heart chamber. A conduit may be placed in the channel to form a blood flow path or the channel itself may form the path.

In another embodiment, the invention provides a device and method for removing a portion of the wall of a coronary vessel located adjacent the wall of a patient's heart. This embodiment includes a shaft and a tissue-removing mechanism disposed at a predetermined distance with respect to the shaft. The shaft is placed adjacent the wall of a coronary vessel and the tissue-removing mechanism is positioned against the wall of the coronary vessel. An actuator coupled to the tissue-removing mechanism is actuated to remove a portion of the wall of the coronary vessel without removing a substantial portion of the wall of the heart located adjacent the coronary vessel.

In another embodiment, the invention provides a device and method for forming a channel through at least a portion of the wall of a patient's heart by utilizing electrical energy. This embodiment includes a shaft and an electrode disposed adjacent a distal end of the shaft. The electrode is adapted to apply electrical energy to tissue in order to ablate the tissue and is coupled to a source of electrical energy, preferably RF (radiofrequency) energy.

BRIEF DESCRIPTION OF THE DRAWINGS

The invention will be better understood from the following detailed description of preferred embodiments thereof, taken in conjunction with the accompanying drawing figures, wherein:

FIG. 3 is a perspective view of a conduit placement device constructed according to one embodiment of the invention, wherein the device includes a sheath shown in a forward position;

FIG. 4 is a longitudinal sectional view of the device shown in FIG. 3;

FIGS. 6A–6C are elevation views, in section, sequentially illustrating the use of the conduit placement device shown in FIG. 3 to place a conduit in the wall of a patient's heart, wherein FIG. 6C shows the conduit positioned in the heart wall;

FIG. 7 is a perspective view of a conduit placement device constructed according to another embodiment of the invention;

FIG. 8 is a longitudinal sectional view of the device shown in FIG. 7;

FIGS. 9A–9G are elevation views, in section, sequentially illustrating the use of the conduit placement device shown in FIG. 7 to place a conduit in the wall of a patient's heart, wherein FIG. 9G shows the conduit positioned in the heart wall;

FIGS. 10A–10C are detailed elevation views, in section, illustrating the positioning mechanism of the conduit placement device shown in FIG. 7 being used to position a conduit in a heart wall, the views corresponding to FIGS. 9A–9C;

FIG. 11 is a perspective view of a conduit placement device constructed according to yet another embodiment of the invention;

FIG. 12 is a longitudinal sectional view of the device shown in FIG. 11;

FIGS. 13A–13F are elevation views, in section, sequentially illustrating the use of the conduit placement device shown in FIG. 11 to place a conduit in the wall of a patient's heart, wherein FIG. 13F shows the conduit positioned in the heart wall;

FIGS. 15A–15F are elevation views, in section, of a tissue removal device constructed according to one embodiment of the invention, wherein the Figures sequentially illustrate the device being used to remove tissue from the wall of a patient's heart;

DETAILED DESCRIPTION OF THE PREFERRED EMBODIMENT

The invention provides methods and devices for delivering a conduit through a coronary vessel and the wall of a patient's heart to place the conduit in communication with a heart chamber, as well as methods and devices for removing tissue from a coronary vessel or the heart wall. It should be noted that, as used herein, coronary vessel refers to any vessel in the vascular structure of the heart, including arterial structures such as coronary arteries and septal perforators. Thus, it will be understood that the LAD 30 illustrated in the Figures is but one example of a possible vessel that may be placed in communication with a heart chamber.

Similarly, in the preferred embodiments the coronary vessel is placed in communication with a heart chamber that contains oxygenated blood, i.e., blood containing some level of oxygen. In the illustrated embodiments the conduit is placed in communication with the left ventricle 12. It will be understood, however, that the methods and devices of the invention may be used to place a conduit in communication with any source of blood (arterial or venous), for example, another heart chamber such as the left atrium, the aorta and pulmonary veins.

Figure 1:
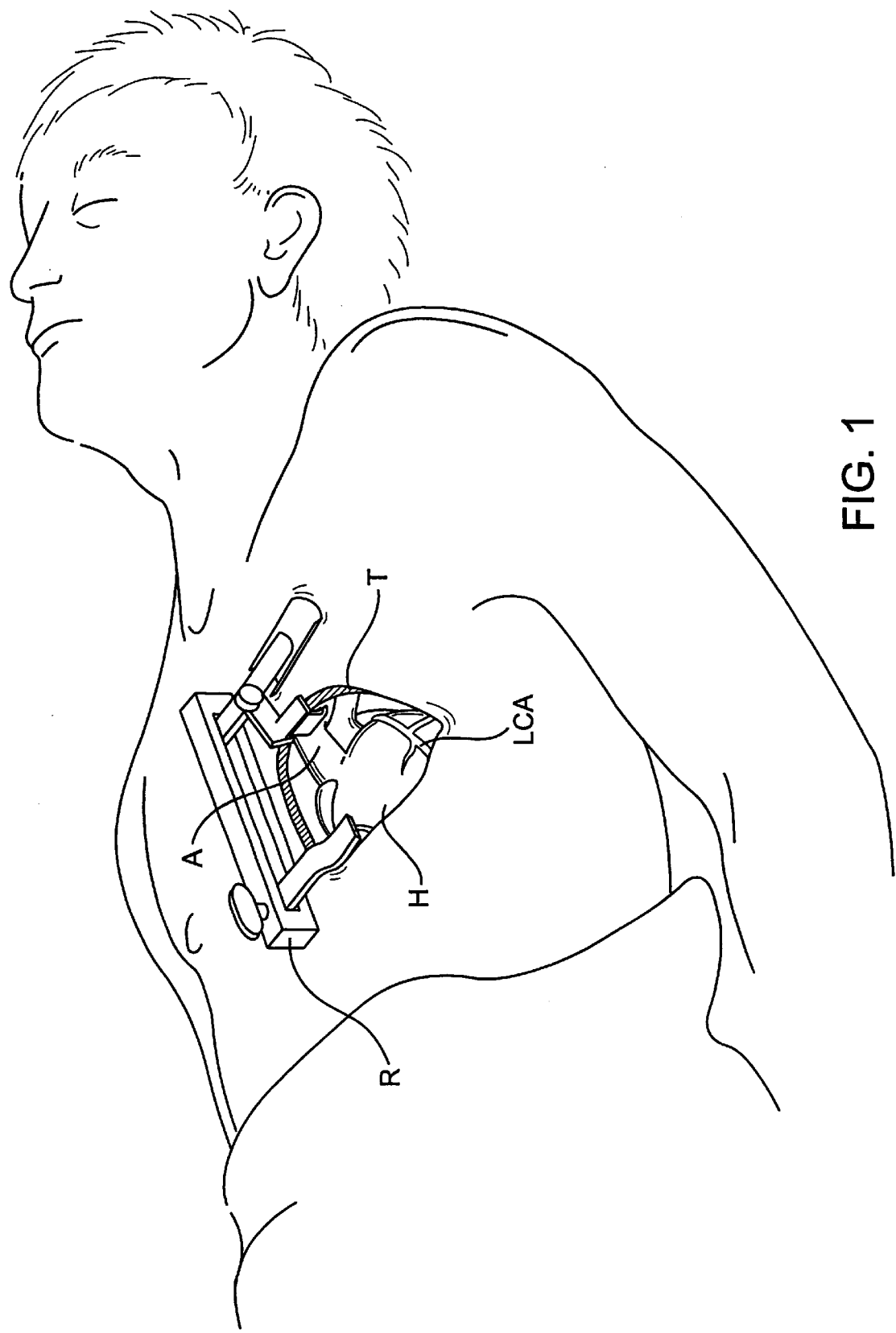
FIG. 1 is a schematic view of a patient prepared to undergo a cardiovascular surgical procedure, the patient's heart being exposed via a retractor positioned in a thoracotomy formed in the patient's chest.

FIG. 1 schematically depicts a patient who has been prepared to undergo a cardiovascular surgical procedure. A thoracotomy T formed in the patient's chest by making an incision between two ribs (not shown) provides access to the thoracic cavity. A retractor, such as the rib retractor R shown in FIG. 1, may be used to spread the ribs and increase access to the heart H and great vessels. The retractor is preferably of a type that in addition to spreading the sides of the incision along a first plane, also raises one side of the incision with respect to the other side to increase the working space around the heart. Any suitable retractor may be used, for example, one of the commercially available rib retractors currently used in minimally invasive cardiac surgery. As shown in FIG. 1, the retractor R provides considerable access to the surfaces of the heart H and great vessels including the aorta A. The left side of the heart as well as the left coronary artery LCA is easily accessible via the thoracotomy T (FIG. 1).

Figure 2:
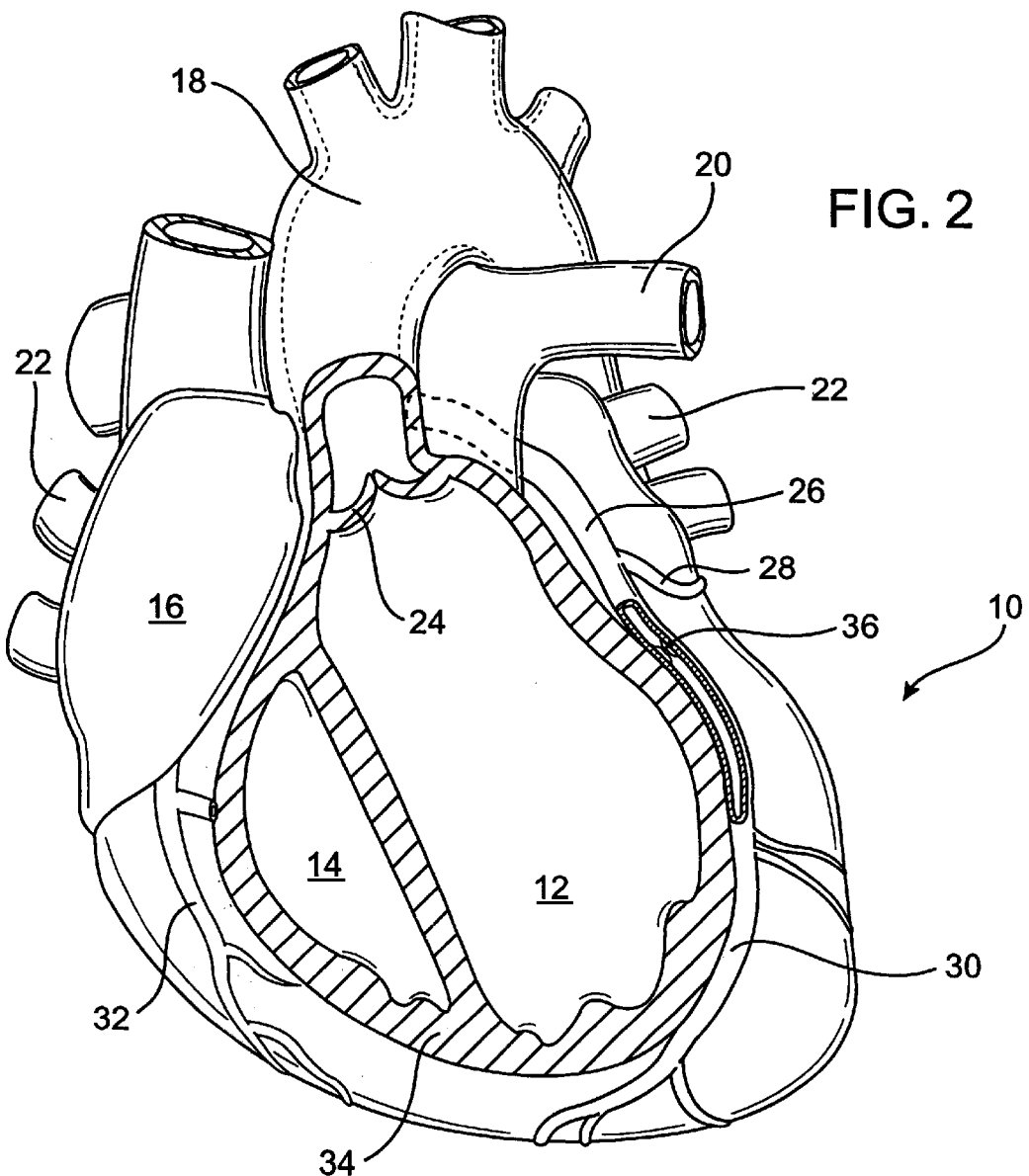
FIG. 2 is a perspective view of the heart shown in FIG. 1, wherein a portion of the heart wall is broken away for clarity.

FIG. 2 is an anterior view of a heart 10 showing the left ventricle 12, right ventricle 14, right atrium 16, aorta 18, pulmonary trunk 20 and pulmonary veins 22. In FIG. 2 the heart 10 is in diastole, or the relaxed phase of the heart cycle, so the aortic valve 24 is shown closed. The left coronary artery 26, including the circumflex branch 28 and the left anterior descending branch (LAD) 30, is visible in this view, as is the right coronary artery 32. The coronary arteries 26, 28, 30, 32 run along the heart wall 34 and deliver oxygenated blood to the tissue comprising the heart wall (epicardium, myocardium and endocardium) while the coronary veins run alongside the arteries and return blood to the coronary sinus (not shown).

Figure 2A:
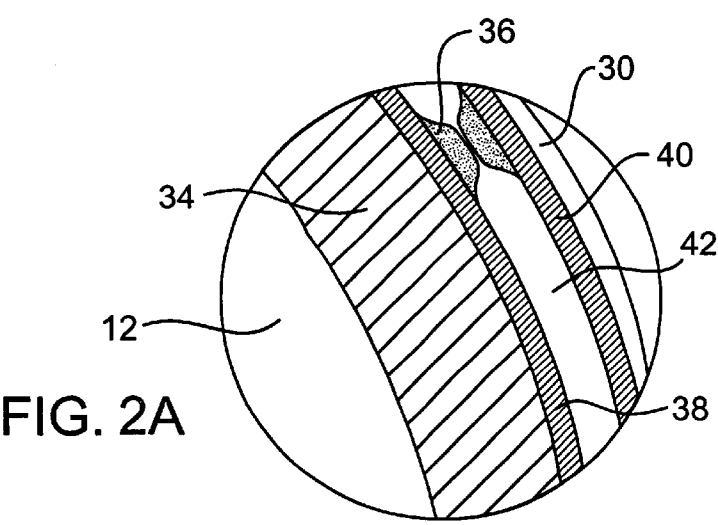
FIG. 2A is an enlarged view of a portion of FIG. 2.

A blockage or occlusion 36 is shown in the LAD 30 and results in partial or complete obstruction of the artery lumen 42, a condition often referred to as narrowing of the arteries. This results in inadequate or no blood flow to the heart wall tissue fed by the portion of the LAD 30 that is downstream of the occlusion 36. FIGS. 2–2A show a portion of the heart wall 34 disposed between the left ventricle 12 and the LAD 30, as well as the inner and outer walls 38, 40 of the LAD 30. The devices and methods of the different embodiments of the invention are illustrated and described in connection with their use on the portion of the heart 10 shown in FIG. 2A. It will be understood, however, that such description is for explanatory purposes and exemplifies only one application for the invention.

Figure 5:
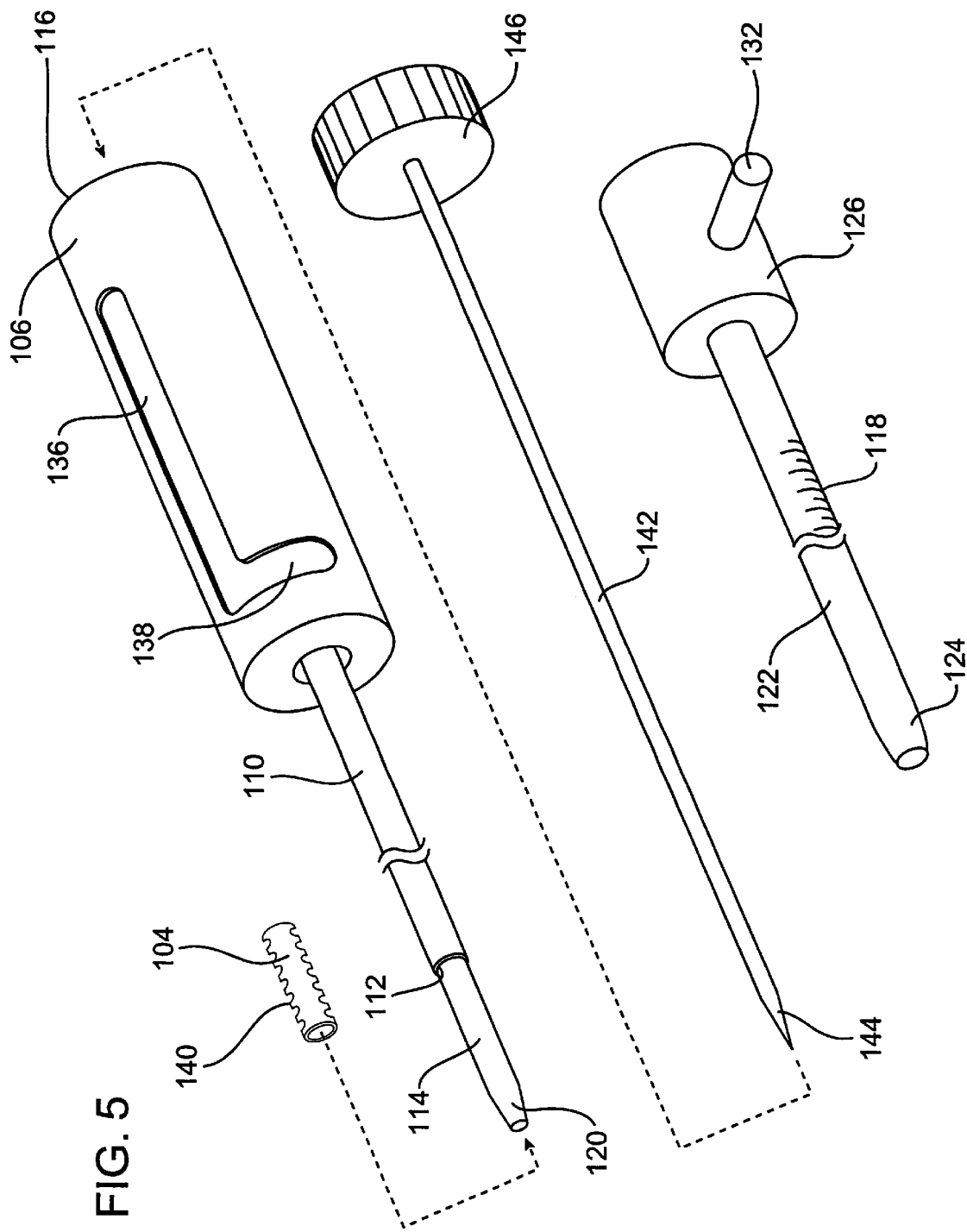
FIG. 5 is a perspective, exploded view of the device shown in FIG. 3.

FIGS. 3–5 illustrate a conduit delivery device according to one embodiment of the invention. The delivery device is indicated by the reference numeral 100 and includes a conduit support member 102, a conduit 104, a housing 106 and an actuator 108. The conduit support member 102 is configured to support the conduit 104. For example, the conduit support member 102 may be in the form of a shaft having a step 112 which defines a recessed portion 114 that receives the conduit 104 (FIGS. 4–5).

The conduit support member 102 is preferably fixed with respect to the housing 106. This allows the position of the conduit 104 to be controlled by controlling the position of the housing 106. As an example, the conduit support member 102 could be attached to the housing 106, or, as shown, the conduit support member 102 could be integrally formed with and extend away from a rear portion 116 of the housing 106 (FIG. 4).

This embodiment of the invention may include means for positioning the conduit at a desired location within the heart wall. For example, the device 100 may be provided with markings 118 to indicate the position of the conduit support member 102 and conduit 104 within the heart wall. Of course, other means of indexing the position of the conduit could be used if desired. The conduit support member 102 preferably has a dilating portion 120 at its distal end forward of the conduit 104 to aid in introducing the device 100.

According to this embodiment of the invention, the device 100 includes a sheath that covers all or a part of the conduit 104 to protect tissue and/or the conduit during its delivery into the heart wall. In the illustrated construction, the device 100 includes a sheath 122 that is sized to engage the exterior of the conduit 104 in a relatively tight friction fit. The sheath 122 has a distal portion 124 disposed over the conduit 104 and a proximal portion 126 disposed within the housing 106. The distal sheath portion 124 preferably is tapered to aid in dilating the opening in the tissue. The proximal sheath portion 126 is preferably enlarged and has a surface 128 that confronts a surface 130 of the housing 106 to prevent the sheath from disengaging the housing. The sheath portion 126 is essentially captured between the housing 106 and the conduit support member 102.

If the conduit support member 102 is formed integrally with the housing 106 as shown, the sheath 122 may be placed within the housing 106 prior to final assembly of the housing. For example, the housing 106 and conduit support member 102 could comprise two sections that are secured together after placing the conduit support member 102 therein. Alternatively, the conduit support member could be a separate component placed in the housing 106 and secured thereto. The housing 106 and the conduit support member 102 may be formed of any suitable material, for example, metals such as stainless steel or titanium, polymers or composite materials.

The sheath 122 preferably comprises a sleeve formed of a material that is relatively strong and flexible so as to engage the conduit 104 and retain it in position on the conduit support member 102. The sheath 122 overlies the conduit 104 to minimize damage due to interaction between the conduit and body tissue during introduction of the device into the patient's heart. The sheath 122 snugly surrounds the conduit 104 but is formed of a material that permits the sheath to be retracted by being forced over the conduit. For example, the sheath may be formed of any suitable strong material that is relatively thin but strong, such as polyimide or stainless steel.

The sheath 122 is retracted to expose the conduit 104 once the conduit has been properly located in the heart wall. The sheath 122 may be retracted manually by moving it in a proximal direction or, as in the preferred embodiment, an actuator may be used to retract the sheath. The illustrated actuator 108 comprises the enlarged portion 126 of the sheath 122 from which a post 132 projects, a spring 134 disposed between the surface 128 of sheath 122 and the surface 130 of housing 106, and a slot 136 in the housing 106.

The actuator 108 allows the sheath 122 to be selectively moved to expose the conduit 104. In FIG. 3, the sheath 122 is in its forward (or distal) position. The spring 134 is captured between the surfaces 128, 130 and biases the sheath portion 126 in a proximal direction; however, due to the post 132 being located in a transverse section 138 of the slot 136, the sheath 122 remains in its forward position. In order to retract the sheath, the post 132 is moved out of the slot section 138 which allows the spring 134 to force the sheath portion 126 in a proximal direction. This moves the entire sheath 122 in a proximal direction (to the right in FIG. 4) and uncovers the conduit 104.

The conduit 104 is a tubular element formed of an implantable, substantially rigid material. Suitable materials include, for example, titanium or stainless steel. The illustrated conduit 104 has a plurality of openings 140 passing through the conduit wall (FIG. 5). The openings 140 form edges along the length of the conduit 104 that contact the tissue of the heart wall to aid in anchoring the conduit in position. The tissue of the heart wall engages these edges as well as the openings 140 to permanently fix the conduit 104 in position.

In addition to the conduit support member 102 and the sheath 122, the device 100 preferably includes a dilator 142 (FIGS. 4–5) having a sharpened end 144 with a dilating portion, and an enlarged end 146 configured to be grasped to manipulate the dilator. The dilator 142 is inserted into the conduit support member 102 so that the end 144 projects beyond the distal ends of the support member 102 and the sheath 122. The end 144 is pushed through the tissue of the coronary vessel and the heart wall to form an opening to receive the conduit 104. Alternatively, the distal end 120 of the conduit support member 102 may include a sharpened edge and a dilating portion for forming an opening in the vessel and heart wall. It should be recognized that the dilator 142 is optional and may be omitted or replaced with a needle or other incising instrument. Further, instead of dilating an incision in the tissue, a channel may be formed in the heart wall and the vessel wall and the conduit positioned in the channel.

FIGS. 6A–6C show one possible application for the conduit delivery device 100, namely, placing a conduit in the wall of a patient's heart so that the conduit communicates a coronary vessel with a heart chamber. Referring to FIG. 6A, the dilator 142 is positioned in the device 100 so that the end 144 of the dilator extends slightly beyond the distal end of the conduit support member 102 and the sheath 122. Next, the device 100, with the sheath 122 overlying the conduit 104, is passed through the walls 38, 40 of the LAD 30 and through the heart wall 34. The device 100 is then moved to a desired position with respect to the heart wall, such as the position shown in FIG. 6A.

As mentioned above, this embodiment of the invention may include means for determining the position of the conduit 104 relative to the heart wall 34. The markings 118 on the sheath 122 are used to position the device 100 (and in particular the conduit support member 102) at the desired location, i.e., the location that places the conduit 104 at a desired position in the heart wall 34. The markings 118 may be read with respect to the outer wall 40 of the LAD 30 or the heart wall 34 in order to position the conduit 104. For example, the most distal marking could be located a predetermined distance from the proximal end of the conduit 104 so that the position of the conduit can be determined by noting the position of this (or any other) marking.

It should be recognized that the markings 118 represent only one means for placing the conduit at a desired location; various alternative positioning mechanisms may be used. In addition, while this embodiment comprises markings on the sheath 122, it will be understood that the markings (or other positioning mechanism) may be carried by another component of the device 100. Also, while in the illustrated embodiment the device includes both a sheath for covering the conduit and a positioning mechanism for correctly positioning the conduit, it will be understood that delivery devices constructed according to this embodiment of the invention may include only one of the sheath and positioning mechanism.

The device 100 and dilator 142 are passed through the walls of the LAD 30 and the heart wall 34 as shown in FIG. 6A. It may be desirable in some applications to support the wall of the coronary vessel while introducing the device in order to ensure passage through the true lumen of the coronary vessel. Access to the coronary vessel may be facilitated by supporting the wall of the vessel by any of the devices and methods disclosed in co-pending, commonly owned application U.S. application Ser. No. 09/172,098, filed on Oct. 13, 1998, and entitled "DEVICES AND METHODS FOR USE IN PERFORMING TRANSMYOCARDIAL CORONARY BYPASS," the disclosure of which is incorporated herein by reference.

With the device positioned as shown in FIG. 6A, the actuator 108 is used to retract the sheath 122 and expose the conduit 104, which results in the device being oriented as shown in FIG. 6B. In this embodiment, the conduit 104 is positioned so that its respective ends project slightly into the lumen 42 of the LAD 30 and the left ventricle 12. Alternatively, the ends of the conduit 104 may be flush, respectively, with the surfaces of the LAD inner wall 38 and the heart wall 34. If placed in proximity to an occlusion (such as occlusion 36) the end of the conduit 104 that is disposed in the artery may by flush with the surface of the occlusion. After the conduit 104 has been positioned as shown in FIG. 6B, the dilator 142 and the device 100 are removed from the conduit 104. This leaves the conduit positioned as shown in FIG. 6C.

The conduit 104 communicates the lumen 42 of the LAD 30 with the interior of the left ventricle 12. As a result, oxygenated blood flows from the ventricle 12, through the conduit 104 and into the LAD lumen 42. The conduit 104 is rigid enough to resist the compressive forces exerted by the heart wall 34 when the heart 10 contracts during systole. The conduit 104 thus remains open during both the systolic and diastolic phases of the heart 10. As mentioned above, a distal end of the conduit 104 (FIG. 6C) preferably extends a slight distance beyond the endocardial surface of the heart wall 34 into the left ventricle 12. This prevents or reduces the likelihood of tissue moving over the distal end of the conduit and reducing or blocking flow from the ventricle 12 into the conduit. Also as mentioned above, a proximal end of the conduit 104 preferably extends a slight distance beyond the inner wall 38 into the lumen 42 of the LAD 30. This prevents or reduces the likelihood of tissue moving over the proximal end of the conduit and reducing or blocking flow from the conduit into the LAD 30. Nevertheless, as noted above, the ends of the conduit may be positioned at various locations with respect to the heart wall 34 and the LAD 30.

The dimensions of the device 100 may vary depending on the application or the user's preferences. For instance, if the device is to be used in a minimally invasive, laparoscopic-type procedure, then the device would have a length sufficient to reach the heart through ports, as opposed to a shorter instrument designed to be used via a thoracotomy as shown or in an open surgical procedure. As an example, for the illustrated application, the overall length of the device 100 may be in the range of from about 4 to 6 inches. The diameters of the components of the device 100 are preferably as small as possible to minimize the size of the opening in the coronary vessel; however, the size of the device may be dictated to a certain extent by the specific size and configuration of the conduit. If used to place a conduit having a diameter within a range of from about 0.080 inch to about 0.120 inch and a wall thickness of 0.005 inch or less, the conduit support member would have an outside diameter sized slightly smaller than the inside diameter of the conduit, while the sheath would have an inside diameter slightly larger than the outer diameter of the conduit.

FIGS. 7–8, 9A–9D and 10A–10C illustrate a conduit delivery device constructed according to another embodiment of the invention. The delivery device is indicated by the reference numeral 148 and has a construction that is basically the same as described above with respect to the previous embodiment. As such, like reference numerals are used to designate like components of the devices. The conduit delivery device 148, however, includes an alternative mechanism for positioning the conduit at a desired location in the heart wall.

In particular, as shown in FIGS. 7–8, the delivery device 148 includes a positioning mechanism 150 disposed adjacent the distal end of the device. The positioning mechanism 150 is preferably in the form of an expandable member that may be introduced into the heart wall in a collapsed orientation and then expanded to an expanded orientation. The sheath 122 preferably covers all or a major portion of the positioning mechanism 150. In the illustrated embodiment, the positioning mechanism 150 includes a plurality of flexible struts 152 disposed circumferentially around the distal end of the device. Each strut 152 has one end 154 attached to the dilator 142 adjacent the end 144 of the dilator. An opposite end 156 of each strut 152 is attached to the conduit support member 102 adjacent the end 120 thereof. The struts may be formed of any suitable flexible material, such as stainless steel or nitinol. The ends 154, 156 of the struts 152 may be attached to the dilator 142 and the conduit support member 102 by any suitable means, for example, welding, brazing, adhesive, or a one-piece construction could be used with the struts integrally formed as part of the dilator and/or support member.

As shown in FIG. 9A, the device 148 is positioned through the coronary vessel and the heart wall 34 by pushing the end 144 of the dilator 142 through the tissue, the dilating portions 120, 124 of the conduit support member 102 and the sheath 122 helping to facilitate passage of the device through the tissue. The device 148 preferably extends into the heart chamber (e.g., left ventricle 12) a sufficient distance to ensure that positioning mechanism 150 is located within the chamber. At this point the positioning member 150 is ready to be expanded and used to position the conduit 104.

Next, the sheath 122 is retracted to uncover the positioning mechanism 150, and in particular the struts 152 thereof (unless the device is introduced with the positioning mechanism 150 uncovered). The sheath 122 may be retracted in one step to uncover both the positioning mechanism 150 and the conduit 104. However, it is preferred to uncover the struts 152 of the positioning mechanism 150 first and maintain the conduit 104 covered until it has been placed in its final desired position, thereby avoiding moving the exposed conduit 104 against the tissue. Therefore, the preferred and illustrated positioning mechanism 150 is actuated in two steps.

The first step retracts the sheath 122 to the position shown in FIG. 9B in order to expose the struts 152 of positioning member 150. This is done by moving the post 132 out of the slot section 138 and into the slot 136 to allow the spring 134 to force the sheath 122 in a proximal direction (FIG. 7). In the illustrated embodiment, the slot 136 includes a second transverse section 158 which forms a stop for the post 132. Thus, the spring 134 drives the sheath 122 away from the distal end of the device until the post 132 is stopped by the slot section 158. The relative dimensions of the device 148 are such that when the post 132 has moved into the slot section 158, the sheath 122 has moved an amount sufficient to uncover all (or a portion of) the positioning mechanism 150. This allows actuation of the positioning member 150 in order to expand the struts 152. After this, the entire device 148 is moved proximally until the positioning member 150 engages the endocardial surface of the heart wall 34, which results in the device being oriented as shown in FIG. 9C.

With the positioning mechanism 150 engaging the heart wall as shown in FIG. 9C, the conduit 104 is positioned so that its respective ends project slightly into the lumen 42 of the LAD 30 and the left ventricle 12. Alternatively, as explained above, the ends of the conduit 104 may be flush with the LAD inner wall 38 and the heart wall 34, or, if placed in proximity to an occlusion 36, the end of the conduit 104 that is disposed in the artery may by flush with the surface of the occlusion. After the device 148 has been positioned as shown in FIG. 9C, the sheath 122 is further retracted to expose the conduit 104, as shown in FIG. 9D.

This step is performed by moving the post 132 out of the slot section 158 and into an axially extending slot section 160, shown best in FIG. 7. This results in the spring 134 driving the sheath 122 proximally to uncover the conduit 104, as shown in FIG. 9D. It will be appreciated that the slot sections 136, 138, 158, 160 comprise only one possible means for controlling retraction of the sheath 122. For example, instead of using a transverse slot section as a stop for the post 132, an alternative construction could use a single axial slot and one or more detents that form stops for the post. The detents could be spring loaded such that the post 132 is prevented from moving past the detent until the detent is depressed. Other mechanisms, of course, could be used as well.

From the position shown in FIG. 9D, the positioning mechanism 150 is moved to its collapsed orientation in which the struts 152 are generally straight, as shown in FIG. 9E. This collapsed, low profile orientation permits the conduit support member 102 and the positioning mechanism 150 to be removed through the conduit 104. FIG. 9F shows the device 148 in the process of being removed through the conduit 104, while FIG. 9G shows the conduit 104 positioned in the heart wall 34 after the device has been removed.

FIGS. 10A–10C are detailed views (in which the sheath 122 has been omitted for clarity) showing the positioning mechanism 150 and the manner in which the mechanism places the conduit 104 in a desired position. The positioning mechanism 150 is actuated by moving the ends 154, 156 of each strut 152 toward each other (to expand the mechanism) or away from each other (to collapse the mechanism). FIG. 10A shows the mechanism 150 in its collapsed orientation wherein the struts extend in a generally linear direction between the conduit support member 102 and the dilator 142. The device 148 is introduced in this collapsed orientation to minimize the size of the opening in the coronary vessel and the heart wall.

In order to expand the positioning mechanism 150, the dilator 142 is moved proximally with respect to the conduit support member 102 and the housing 106. In the illustrated embodiment, the dilator 142 is retracted by grasping the enlarged portion 146 with one hand while holding the housing 106 in the other hand. This moves the ends 154, 156 of the struts 152 toward each other which causes the struts to expand in a radially outward direction, as shown in FIG. 10B. At this point the positioning mechanism 150 is expanded, however, the conduit 104 is not located in the desired position; rather, as shown in FIG. 10B, the conduit 104 extends too far into the left ventricle 12.

The positioning mechanism 150 is then used to position the conduit 104 in the desired location in the heart wall by moving the entire device 102A proximally until the struts 152 engage the heart wall 34, as shown in FIG. 10C. The predetermined distance between the mechanism 150 and the conduit is used to determine proper placement, for example, the distance separating the ends of the struts 152 and the distal (ventricle) end of the conduit 104 is selected so that the conduit is in the desired position when the struts are engaged with the heart wall. After this, as explained above with respect to FIGS. 9A–9G, the device 148 is removed leaving the conduit 104 in place.

It should be understood that alternative actuators may be used to move the sheath 122. For example, the sheath 122 could be moved manually to uncover the positioning mechanism 150 and the conduit 104. Also, alternative positioning mechanisms could be used, such as providing the sheath 122 with markings that indicate when the sheath has been retracted an amount that uncovers the positioning mechanism 150 or the conduit 104, or a flashback lumen that indicates when the device has entered the coronary vessel or heart chamber. Additionally, an actuator could be used to carry out the final positioning step of FIG. 10C by moving the entire device 148 to engage the positioning mechanism 150 with the heart wall.

Also, in the embodiment shown in FIGS. 7–10C, the dilator 142 forms part of the actuator in that it is attached to the ends 154 of the positioning struts 152. As such, in this embodiment the dilator 142 is not removed separately from the device 148. Nonetheless, it will be appreciated that a separate, removable dilator could be used, for example, by providing an additional member to which the ends 154 of the positioning struts 152 are attached. The member would then be moved relative to the conduit support member 102 to expand or collapse the positioning mechanism 150.

A conduit delivery device constructed according to yet another embodiment of the invention is shown in FIGS. 11, 12 and 13A–13F. The delivery device is indicated by the reference numeral 170 and, like the embodiment of FIGS. 7–10C, has a construction that is similar to the embodiment of FIGS. 3–6C. Accordingly, like reference numerals are used to designate like components. The device 170, however, includes an alternative mechanism for positioning the conduit at a desired location in the heart wall, as well as an alternative conduit and conduit support member.

The delivery device 170 includes a conduit support member 172 and a conduit 174. According to this embodiment of the invention, the conduit 174 is positioned in the heart wall and then expanded. This embodiment includes an optional sheath 122 that may be used to cover the conduit 174 during introduction into the heart wall for reasons discussed above.

The conduit 174 illustrated in FIGS. 11–12 is expandable and may be in the form of an coronary stent 176 comprising a plurality of struts or filaments 178 that move relative to each other as the stent expands or collapses. The stent 176 may be formed of any suitable material such as stainless steel or titanium, and may include struts as shown or any alternative expandable structure. The stent 176 can be self-expanding and constrained by the sheath 122, or the stent may be expanded by a suitable mechanism. In the illustrated embodiment, an expandable mechanism is carried by the conduit support member 102 and comprises an inflatable balloon 180 around which the stent 176 is disposed. Other expandable mechanisms, inflatable or not, could of course be used.

As shown in FIG. 12, the conduit support member 172 has a recess 182 in which the balloon 180 is mounted, the recess extending between opposite surfaces 184, 186. The stent 176 is mounted on the balloon 180 and the sheath 122 overlies the stent. Also, as shown in FIG. 12, the distal portion of the conduit support member 172 is tapered at 188 to aid in dilating the opening in the tissue to introduce the device 170. As in the above embodiments, the dilator 142, conduit support member 172, and sheath 122 are sized and configured to nest together tightly so as to minimize the outer profile of the device.

This embodiment of the invention, as exemplified by the illustrated device 172, includes an alternative conduit positioning mechanism 190. The mechanism 190 comprises a positioning member 192 in the form of a tubular shaft disposed over a portion of the sheath 122. The positioning member 192 has a proximal end 194 attached to the distal portion of the housing 106, for example, by welding, brazing, adhesive, etc. Alternatively, the positioning member 192 could be formed as an integral extension of the housing 106. The distal end of the positioning member 192 has a stop surface 196 that is configured to contact tissue to gauge the position of the conduit 174.

FIGS. 13A–13F show one possible application for the device 100—placing a conduit in the wall of a patient's heart to communicate a coronary vessel with a heart chamber. As above, the heart chamber preferably contains oxygenated blood and, in the illustrated embodiments is the left ventricle. Also as above, the conduit may be placed in communication with any source of blood, for example, another heart chamber such as the left atrium, the aorta, pulmonary veins, etc.

Figure 13A:
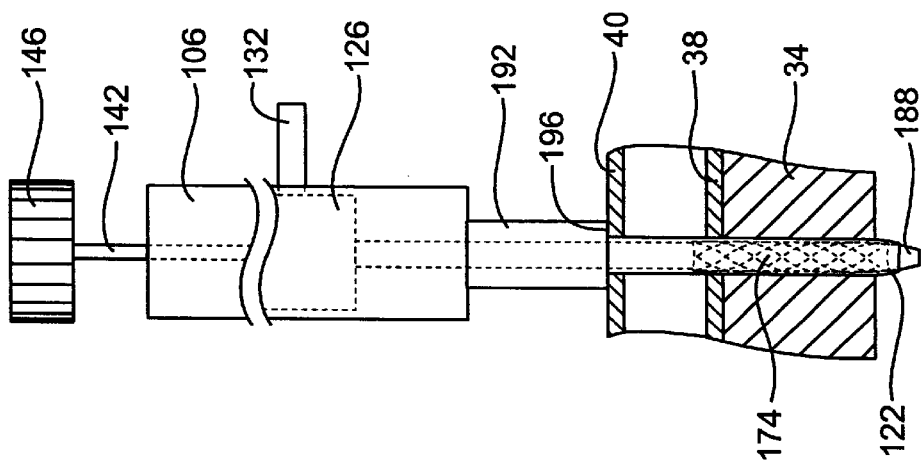
Figure 13B:
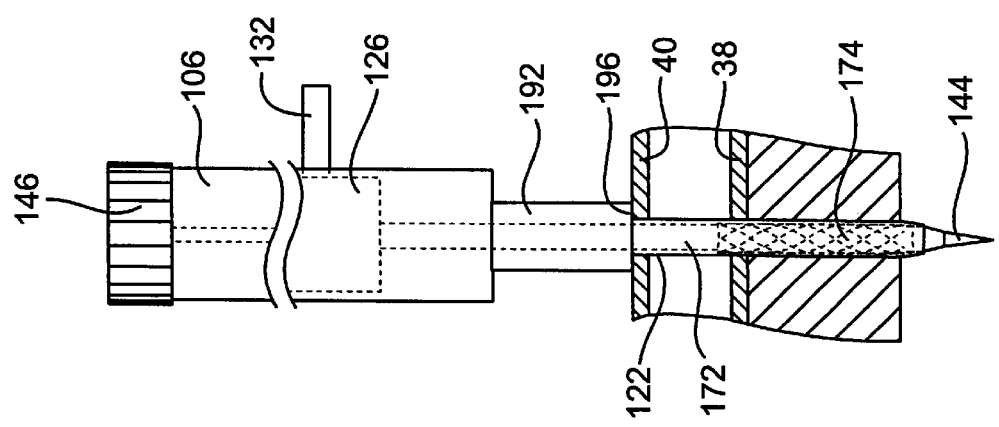
Figure 13C:
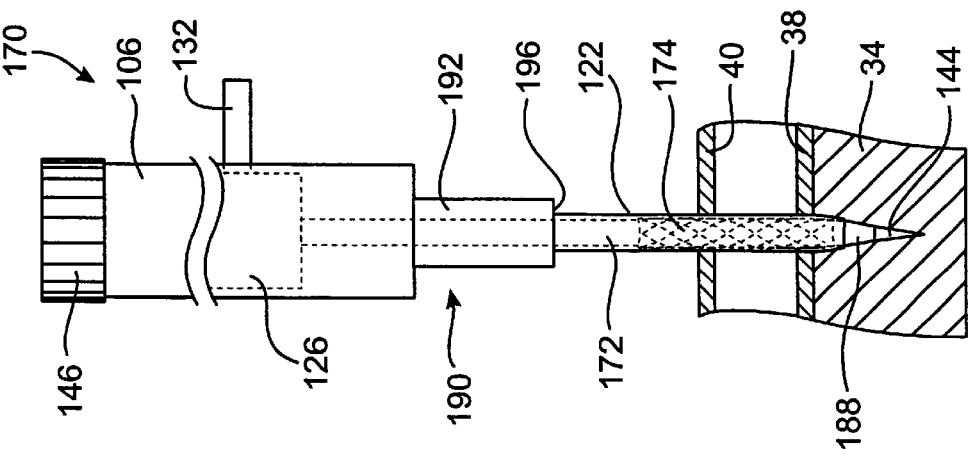

Referring to FIG. 13A, the sharpened end 144 of the dilator 142 is passed through the walls of the LAD 30 and the heart wall 34. The device 170 is moved toward the heart wall 34 until the stop surface 196 of the positioning member 192 contacts the LAD 30, as shown in FIG. 13B. The device 170 is constructed and dimensioned so that when the surface 196 contacts the outer wall 40 of the LAD 30 the stent 176 is in the desired position within the heart wall. For example, the stop surface 196 of the positioning member 192 may be disposed a predetermined distance X from the proximal end of the stent 176, as shown in FIG. 13C. Therefore, locating the stop surface 196 of the positioning member 192 also locates the stent 176 in a desired position (e.g., with the conduit ends in the coronary vessel and the heart chamber, as shown in FIG. 13C).

In this embodiment, the position of the stent 176 with respect to the heart wall is indexed by controlling the position of the member 192 with respect to the heart wall 34. In FIGS. 13A–13F the wall of the LAD 30 remains dilated or distended while the device 170 is passed therethrough. As in the previous embodiment, the wall of the coronary vessel may be supported in a dilated or distended condition by any of the devices and methods disclosed in the aforementioned application, the subject matter of which has been incorporated by reference herein. The positioning member 192 is configured to properly position the stent 176 when the member 192 contacts the wall of the coronary vessel without collapsing the wall. Thus, when in the position shown in FIGS. 13B–13C, the positioning member 192 indicates to the user that the stent 176 is in position and ready to be expanded.

Figure 14:
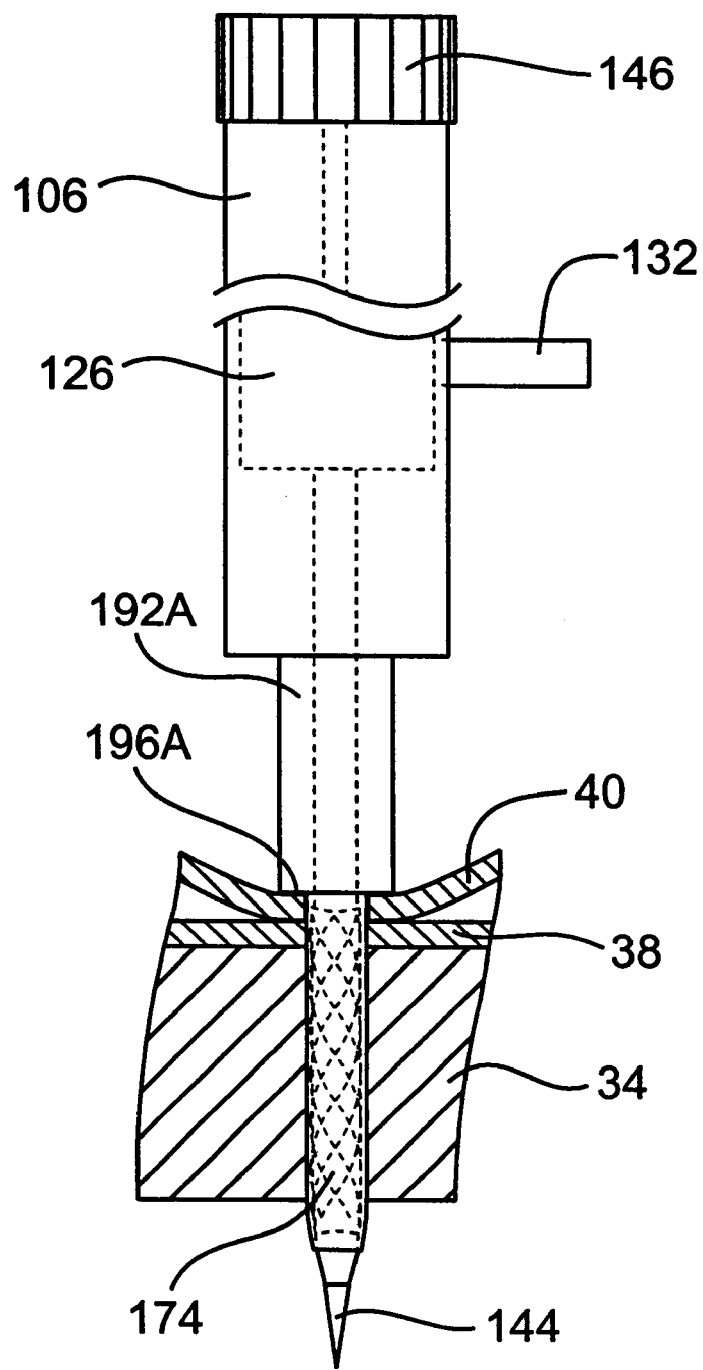
FIG. 14 is an elevation view, in section, illustrating the positioning mechanism of an alternative conduit placement device being used to position a conduit.

Alternatively, as exemplified in FIG. 14, the device 170 may include a positioning member 192A that uses a collapsed wall of the coronary vessel in order to gauge proper placement of the conduit. As shown, the device 170 may be constructed so that the stent 176 (or other conduit) is properly positioned when the positioning member 192A engages the collapsed LAD 30. The distance Y between the stop surface 196A of the positioning member 192A and the stent 176 could again be used to control positioning so that the stent is in the desired position when the wall of the coronary vessel is collapsed.

Returning to FIGS. 13A–13F, when the positioning member 192 is located as shown in FIG. 13B the stent 176 is positioned so that its ends project slightly into the lumen 42 of the LAD 30 and the left ventricle 12. As in the previous embodiments, the ends of the stent 176 may be flush with the surfaces of the LAD wall 38 and the heart wall 34 (or an occlusion such as stenosis 36). From the position shown in FIG. 13B, the dilator 142 is removed from the conduit support member 172, as shown in FIG. 13C. Alternatively, the dilator 142 is not used and the distal end of the conduit support member 172 is formed with an incising/dilating portion for forming an opening in the vessel and the heart wall.

The sheath 122 is then moved to expose the stent 176 which results in the stent struts contacting the tissue of the heart wall 34 and the inner wall 38 of the LAD. The conduit support member 172 is preferably held in position while the sheath 122 is retracted to ensure that the stent 176 remains in proper position. After the sheath 122 has been retracted, the balloon 180 (or other expandable structure) is no longer constrained and may be inflated, as shown in FIG. 13D. The balloon 180 is inflated to expand the stent 108 to its expanded orientation, as shown in FIG. 13E. A suitable source of pressurized fluid such as a syringe pump delivers fluid to the balloon 180 by a lumen (not shown) passing through the conduit support member 172.

The balloon 180 is preferably sized to expand the stent 176 to an orientation that provides the stent with maximum radial strength to resist collapsing. The struts of the expanded stent 176 engage the tissue to aid in fixing the stent in position. With the stent 176 in position and expanded, the balloon 180 is deflated and the conduit support member 172 is removed, leaving the stent 176 positioned in the heart wall as shown in FIG. 3F. As in the previous embodiment, the stent 176 communicates the LAD 30 with the interior of the left ventricle 12 to allow oxygenated blood to flow from the ventricle through the stent and into the lumen of the LAD. The stent 176 is constructed to resist the compressive forces exerted by the heart wall 34 during systole so that the stent remains open during both the systole and diastole. As mentioned above, the ends of the stent 176 preferably extend into the LAD 30 and the left ventricle 12 to reduce the likelihood of tissue occluding the ends of the stent.

FIGS. 15A–15F depict another embodiment of the invention that provides devices and methods for forming an opening through the tissue of a heart wall. The opening is formed to receive a conduit that forms a flow path between a coronary vessel and a heart chamber; alternatively, the opening itself forms a flow path with no conduit being used. Accordingly, the delivery devices and methods described above with respect to the previous embodiments may be used (without a dilator) to place a conduit in a channel or opening formed according to this embodiment. In addition, while the devices and methods according to this embodiment are described and illustrated in connection with forming channels in a heart wall to establish a flow path between a coronary vessel and a heart chamber, it will be appreciated that the devices and methods may be utilized in various other applications.

Turning now to FIG. 15A, a device for forming a channel through tissue is designated generally by the reference numeral 200 and includes a shaft 202 and a tissue removal mechanism 204. The shaft 202 has a proximal end 206 in the form of a hub with a side port 208 which may be coupled to a vacuum source (not shown) with a filter for use in aspirating tissue removed by the device 200. A dilator 210 is positioned in the shaft 202 and has an end 212 configured to incise and dilate an initial opening in the tissue. The device 200 is passed through the wall of the LAD 30 and the heart wall 34 until the distal end of the device is located within the left ventricle 12, as shown in FIG. 15B.

The illustrated embodiment includes a tissue support mechanism for engaging and supporting the heart wall 34 during formation of the channel by the tissue removal mechanism 204. A preferred support mechanism comprises an expandable structure 214 that may be placed in a collapsed orientation (FIGS. 15A–15B) for introduction through the tissue. The expandable structure 214 may be constructed as shown in the Figures, or it may have a construction the same or similar to the tissue engaging instruments disclosed in the aforementioned application, the subject matter of which has been incorporated by reference.

The expandable structure 214 includes a plurality of flexible elements 216 that move away from each other as the mechanism expands. Each of the elements 216 has one end fixed to the dilator 210 and an opposite end fixed to the shaft 202 (the ends not being shown in the Figures). The support mechanism is expanded by retracting the dilator 210 while holding the shaft 202 in place. This moves the ends of the elements 216 toward each other and expands the structure 214 as shown in FIG. 15C. The expandable structure 214 of the support mechanism thus operates in a similar manner to the positioning mechanism 150 of the embodiment shown in FIGS. 11–15.

Figure 15F:
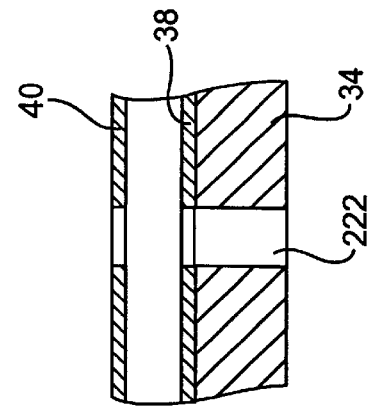
Figure 15E:
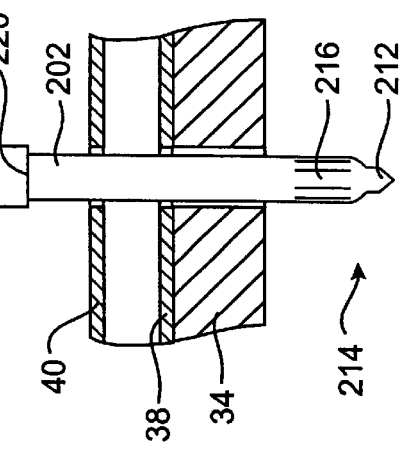
Figure 15D:
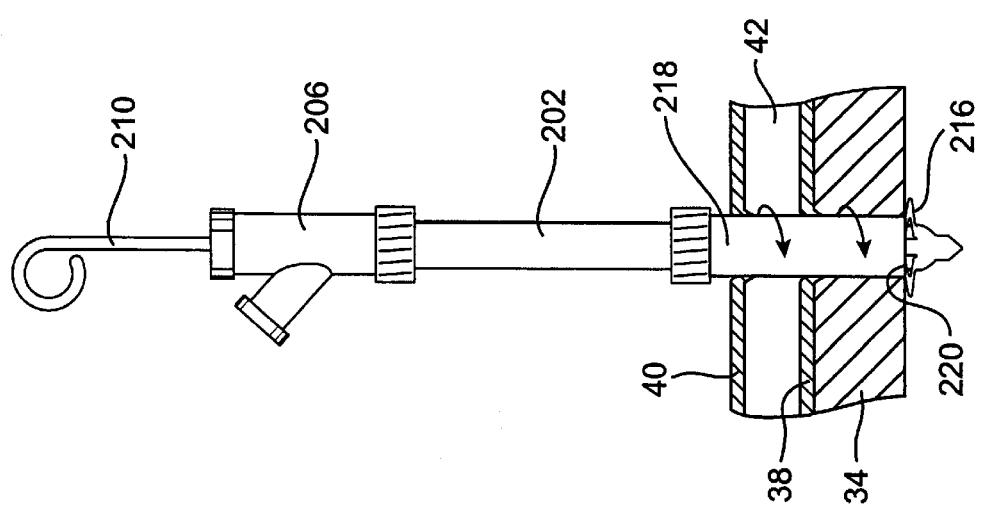

In order to form a channel in the tissue, the expandable structure 214 is used to securely grasp the tissue during engagement by the tissue removal mechanism 204. This is accomplished by moving the expandable structure 214 into engagement with the endocardial surface of the heart wall 34 and retracting the heart wall as shown in FIG. 15C. With the device 200 in this position, the tissue removal mechanism 204 is moved along the shaft 202 into engagement with the coronary vessel and the heart wall, as shown in FIG. 15D. As such, the support mechanism engages the heart wall and acts as a retractor during actuation of the tissue removal mechanism.

The tissue removal mechanism 204 may take various forms and, in the illustrated embodiment, comprises a rotatable coring element 218 with a cutting edge 220 configured to bore a channel 222 in the coronary vessel and the heart wall. It will be recognized that this aspect of the invention may utilize a tissue removal mechanism that forms a channel without utilizing a cutting edge as in the illustrated embodiment. Suitable alternative tissue removal mechanisms may utilize lasers, RF ablation devices, coring devices, drills, etc.

As the coring element 218 moves through the tissue of the heart wall 34 the cutting edge 220 removes a core of tissue to form channel 222. The tissue may simply move into the interior of the coring element 218 as it is cut for subsequent removal with the device. Alternatively, as mentioned above, the removed tissue may be aspirated through the device to a receptacle (not shown). The coring element 218 passes through the tissue and then contacts the struts 216 of the expandable structure 214 of the tissue support mechanism, as shown in FIG. 15D. At this point, the channel 220 has been created and the device 200 may be removed, which is accomplished by collapsing the expandable structure 214 of the tissue-supporting mechanism, as shown in FIG. 15E. The device 200 is then removed leaving the channel 220 passing through the coronary vessel and the heart wall, as shown in FIG. 15F.

The dimensions of the device 200 also will vary depending on the application, as well as the desired size of the channels formed in the heart wall. As above, the size of the device will depend on the intended use of the device, for example, whether the procedure is performed in a minimally invasive manner through ports, through a thoracotomy as shown, or via an open surgical procedure. Also, the device may be used in a different manner than depicted. For example, the device may be passed all or substantially all the way through the heart wall into the chamber, and then moved back through the wall in order to core a channel.

FIGS. 16A–16F depict another embodiment of the invention that provides devices and methods for removing tissue. In its preferred form, this embodiment is used to remove a portion of a body of tissue, for example, a portion of the wall of a coronary vessel. This may facilitate easier placement of a conduit to form a flow path between a coronary vessel and a heart chamber, or it may be used as an initial step in forming a channel that forms such a flow path. In the illustrated embodiment, the device and method are used to remove a section of the inner wall of a coronary vessel in order to place conduit in the heart wall. The walls of coronary vessels, and in particular coronary arteries, are fairly resilient (compared to the tissue of the heart wall) and tend to resist passage of an instrument therethrough. In addition, the tissue of the artery wall may tend to move over and occlude the opening of a conduit (or channel) that communicates with the coronary artery. Thus, this embodiment is useful in forming a reliable opening through the wall of a coronary vessel.

Figure 16A:
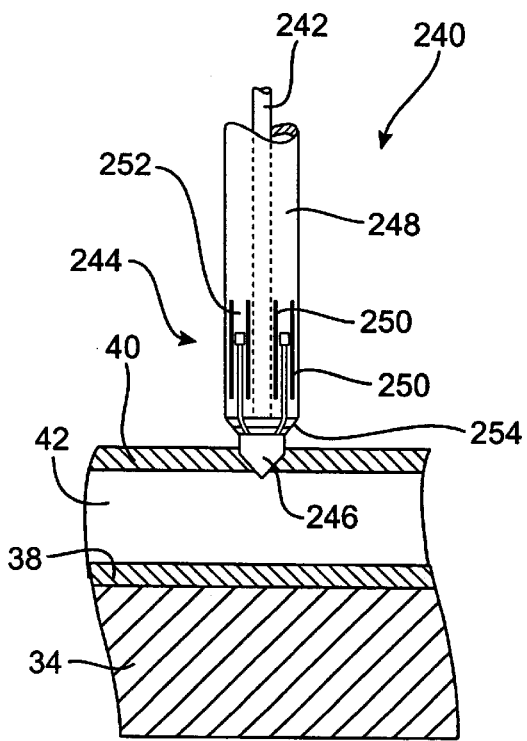
FIGS. 16A–16D are elevation views, in section, of a tissue removal device constructed according to another embodiment of the invention, wherein the Figures sequentially illustrate the device being used to remove tissue from the wall of a coronary vessel.

FIG. 16A shows a preferred device constructed according to this embodiment. The device is indicated generally by the reference numeral 240 and includes a shaft 242 and a tissue removal mechanism 244. The tissue removal mechanism 244 has a construction somewhat similar to the expandable structure 214 of the tissue support mechanism shown in FIGS. 15A–15F it is collapsed for introduction and then expanded in order to engage tissue. The illustrated tissue removal mechanism 244 utilizes electrical energy, preferably RF energy, to ablate selected portions of tissue; however, it should be understood that this embodiment of the invention may be practiced by removing tissue mechanically rather than electrically, for example, by cutting the tissue as shown in FIGS. 15A–15F.

Figure 16B:
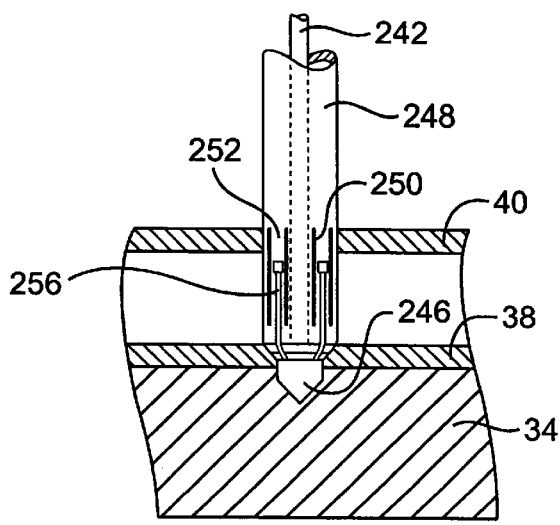

In use, as shown in FIG. 16A, the device 240 is introduced into the lumen 42 of the LAD 30 by passing a sharpened end 246 of the shaft 242 through the outer wall 40 of the LAD. Alternatively, an incision may be formed in the wall of the LAD 30 and the device 240 passed therethrough, the end 246 of the shaft 242 being used simply to dilate the incision. The device 240 is moved through the lumen 42 of the LAD 30 until the tissue removal mechanism 244 contacts the inner wall 38 of the LAD, as shown in FIG. 16B. At this point the mechanism 244 is ready to be actuated.

The tissue removal mechanism 244 comprises a flexible sleeve 248 movable disposed over the shaft 242. The sleeve 248 has a plurality of slits 250 that define a plurality of flexible elements 252 which preferably extend circumferentially around the device. The distal portion 254 of the sleeve 248 is fixed to the shaft 242 such that moving the sleeve toward the end 246 of the shaft expands the mechanism 244 by forcing the flexible elements 252 radially outward. Thus, once the device 240 is placed against the inner wall 38 of the LAD 30, as shown in FIG. 16B, the tissue removal mechanism 244 is actuated by moving the sleeve 248 in a distal direction while holding the shaft 242 stationary. This causes the mechanism 244 to assume the expanded orientation shown in FIG. 16C.

Figure 16C:
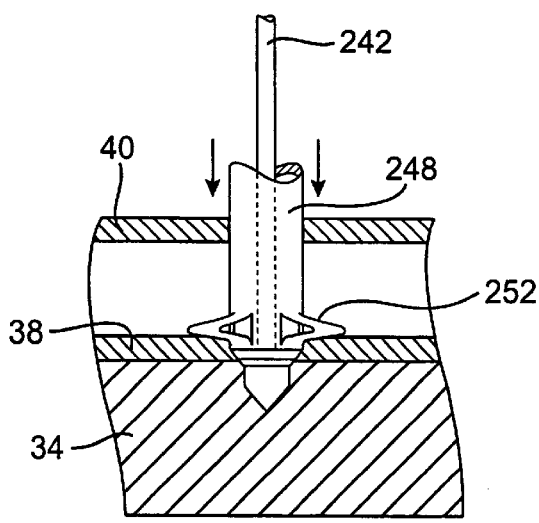

The flexible elements 252 are provided with conductive elements 256 formed of any suitable material capable of conducting electrical energy. The conductive elements 256 are electrically coupled to an RF power source that may be in the form of a suitable generator (not shown). With the mechanism located as shown in FIG. 16C, the source of RF energy is activated and current is fed to the conductive elements 252.

Figure 16D:
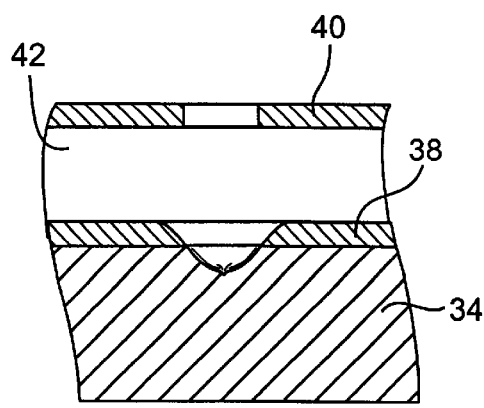

The conductive elements 252 are in contact with the tissue of the inner wall 38 of the LAD 30 so that the current ablates the tissue surrounding the tissue removal mechanism 244. Upon completion of the ablation process, the energy source is deactivated, the tissue removal mechanism 244 is returned to the collapsed orientation shown in FIG. 16B, and the device 240 is removed. This procedure removes a portion of the inner wall 38 of the LAD 30, as shown in FIG. 16D. While in the illustrated embodiment a portion of the wall 38 of the LAD 30 is removed along with a small portion of the heart wall 34, it will be appreciated that this aspect of the invention may be used to remove a portion of the wall of the LAD only. In fact, a portion of the wall of the coronary vessel may be removed along with none or any desired amount of the heart wall. Also, although an expandable tissue removal mechanism is preferred to allow formation of a relatively small opening in the outer wall of the coronary vessel (FIG. 16D), a non-expandable, tissue removal mechanism could be used instead.

The embodiment of the invention shown in FIGS. 16A–16D may be used to form an opening through the inner wall of a coronary artery such as that shown in FIG. 16D. A benefit of using electrical energy to remove the tissue (rather than mechanical removal) is that scar tissue forms along the periphery of the opening in the wall of the artery. The scar tissue, which is visible in FIG. 16D, maintains the opening in the artery wall and minimizes the risk of tissue moving or growing over or into the end of the conduit positioned in the coronary vessel.

As with the previous embodiment, the dimensions of the device 240 will vary depending on the specific application and the amount and size of tissue to be removed. As an example, the device 240 may be used to remove a portion of the wall of a coronary artery that is approximately 1–4 mm in diameter. Further, the device may be used in a different manner than depicted. For example, the device may be passed all or substantially all the way through the heart wall into the chamber, and then moved back a small amount and actuated to remove a section of the endocardial portion of the heart wall. The device would then be moved through the heart wall until the tissue removal mechanism is located adjacent the inner wall of the coronary vessel, at which point the device is actuated to remove a section of the vessel wall.

Figure 17:
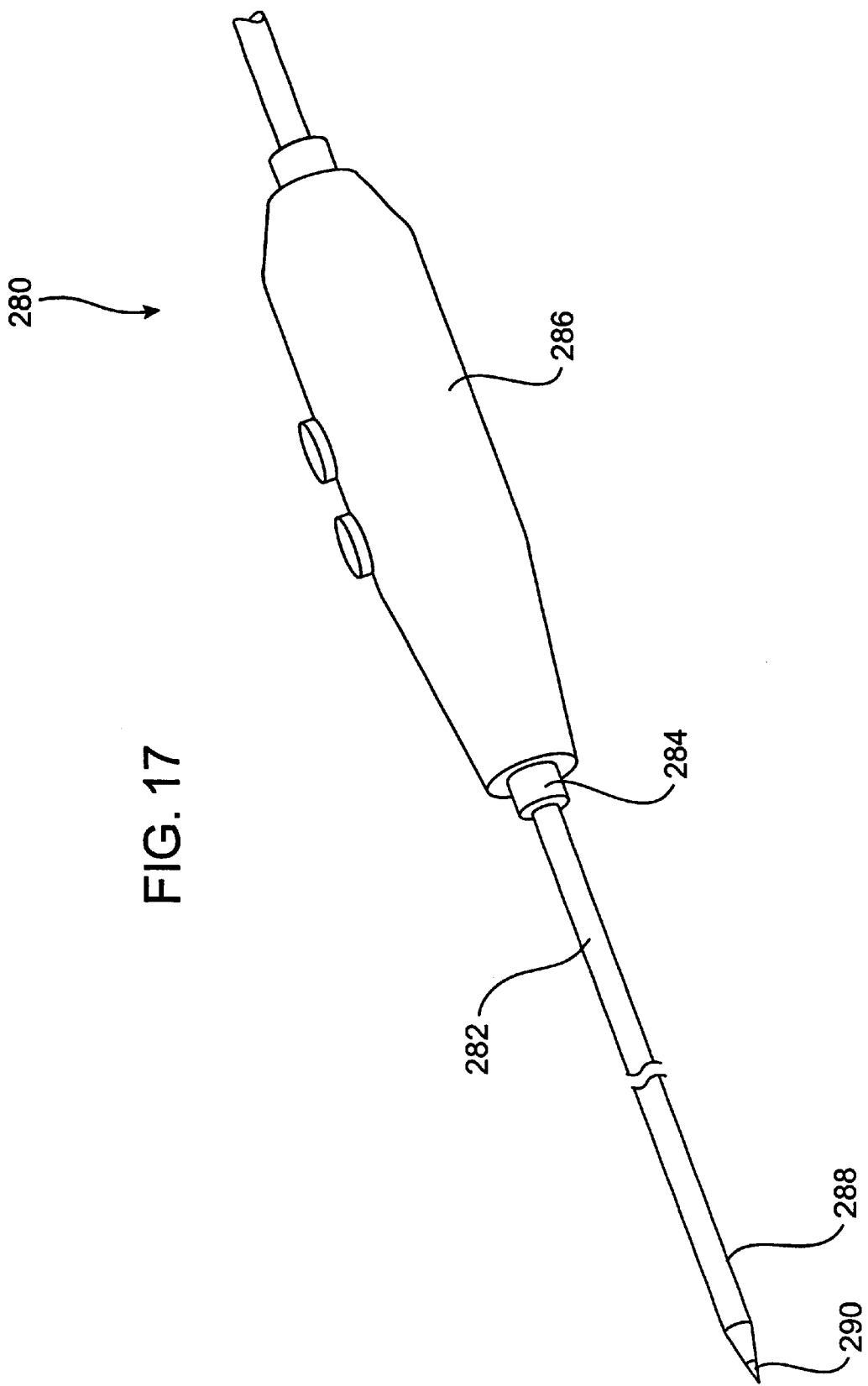
FIG. 17 is a perspective view of a tissue removal device constructed according to yet another embodiment of the invention.
Figure 18C:
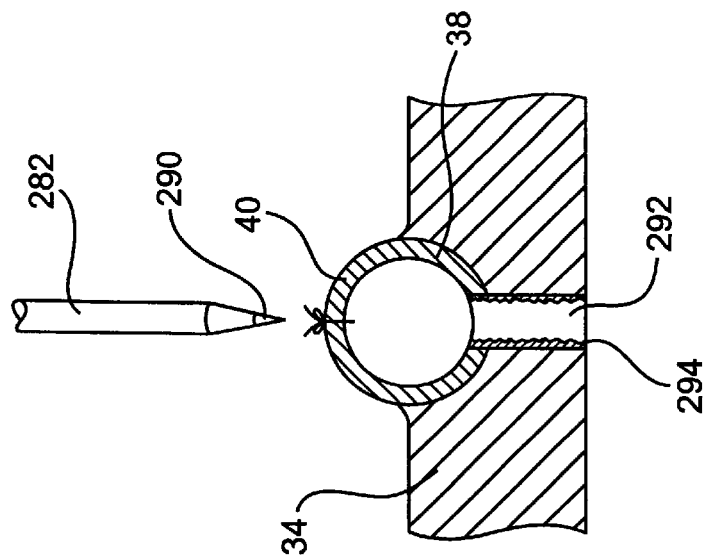
FIGS. 18A–18C are elevation views, in section, illustrating the tissue removal device shown in FIG. 17 being used to remove tissue from the wall of a patient's heart.

FIGS. 17–18C depict another embodiment of the invention that provides devices and methods for establishing an opening through body tissue, the opening preferably defined by a channel formed by electrical energy. This embodiment, in its preferred form, produces an opening defined by surfaces of scar tissue that serve to maintain a patent channel. The devices and methods of this embodiment are preferably used to form a channel through a heart wall that communicates a coronary vessel with a heart chamber.

The illustrated embodiment comprises a channel-forming device indicated generally by the reference numeral 280 in FIG. 17. The device 280 includes a wire electrode 282 formed of a suitable conductive material such as stainless steel. The electrode 282 has a proximal end 284 configured to be attached to a conventional electrocautery instrument 286 (shown in phantom). The electrode 282 is preferably disposable and therefore is removably attached to the electrocautery instrument 286, for example, by a threaded connection, press fit, etc. The proximal end 284 of the electrode 282 receives electrical energy from the instrument 286.

A portion of the electrode 282 is preferably coated with an insulating material 288 so as to leave only the distal portion 290 of the electrode exposed to contact 30 and ablate tissue. The material 288 may be any insulator, for example, polyimide or graphite. As such, the distal portion 290 of the electrode 282 is used to ablate tissue while the remaining portion of the electrode is free to contact tissue without ablating or damaging that tissue.

The dimensions of the channel-forming device 280 may vary depending on the application and the size of the channels to be formed in the tissue. As an example, the proximal end 284 of the electrode 282 may be sized and configured to engage a standard electrocautery pencil, for example, by having an outer diameter of approximately 0.095 inch. The shaft 282 may comprise a wire having an outside diameter of approximately 0.015 inch, while the insulating material 288 has an inside diameter of approximately 0.015 and an outside diameter of approximately 0.025 inch.

Figure 18B:
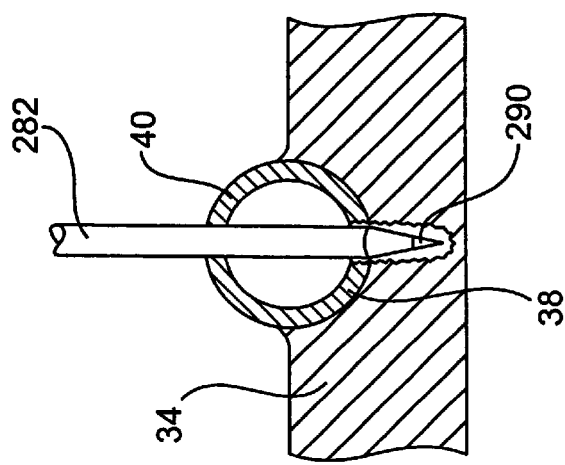
Figure 18A:
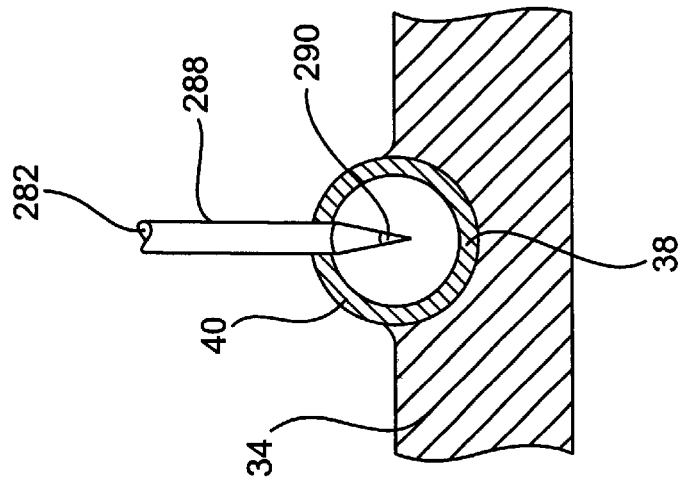

Referring to FIGS. 18A–18C, an exemplary application of this embodiment of the invention will be described. The channel-forming device 280 is placed through the wall of a coronary vessel such as the LAD 30 shown in FIG. 18A. The distal end of the electrode 282 may simply be passed through the wall 40 of the LAD 30 or, alternatively, an opening can be formed in the artery wall and the device introduced through the opening. Once in the position of FIG. 18B, the RF power source is activated and current is conducted through the electrode 182. The exposed portion 290 of the electrode is moved into contact with the tissue of the wall 38 of the LAD 30 and then the tissue of the heart wall 34. The electrode 282 is pushed through the tissue with a relatively small amount of force and the RF energy ablates the tissue as it is moved. The particular amount of energy used may vary, as may the speed and force with which the electrode 282 is moved through the tissue. These variables may be controlled or adjusted to achieve the desired channel size and configuration. As an example, the device 280 may be supplied with 10 watts of energy with the electrocautery instrument in pure cut mode.

Once the device 280 has been passed through the heart wall 34 a sufficient distance to form a channel 292 passing therethrough, the device is removed as shown in FIG. 18C and the opening in the wall 40 of the LAD 30 is repaired. As shown, and as explained above with respect to the embodiment of FIGS. 16A–16D, the ablation of the tissue forms a layer of scar tissue 294 that surrounds the channel 292 and aids in maintaining the channel open over time. Also, while the illustrated embodiment forms a channel passing entirely through the artery wall 38 and the heart wall 34, this aspect of the invention may be used to form a channel that extends only partially through one or both of these respective tissue walls. As explained above with respect the previous embodiments, the dimensions of the device 280 will vary depending on the application and the size of the channel to be formed; for example, the device may be used to form a channel having an approximate diameter in the range of from about 0.100 inch and about 0.200 inch.

Figure 19:
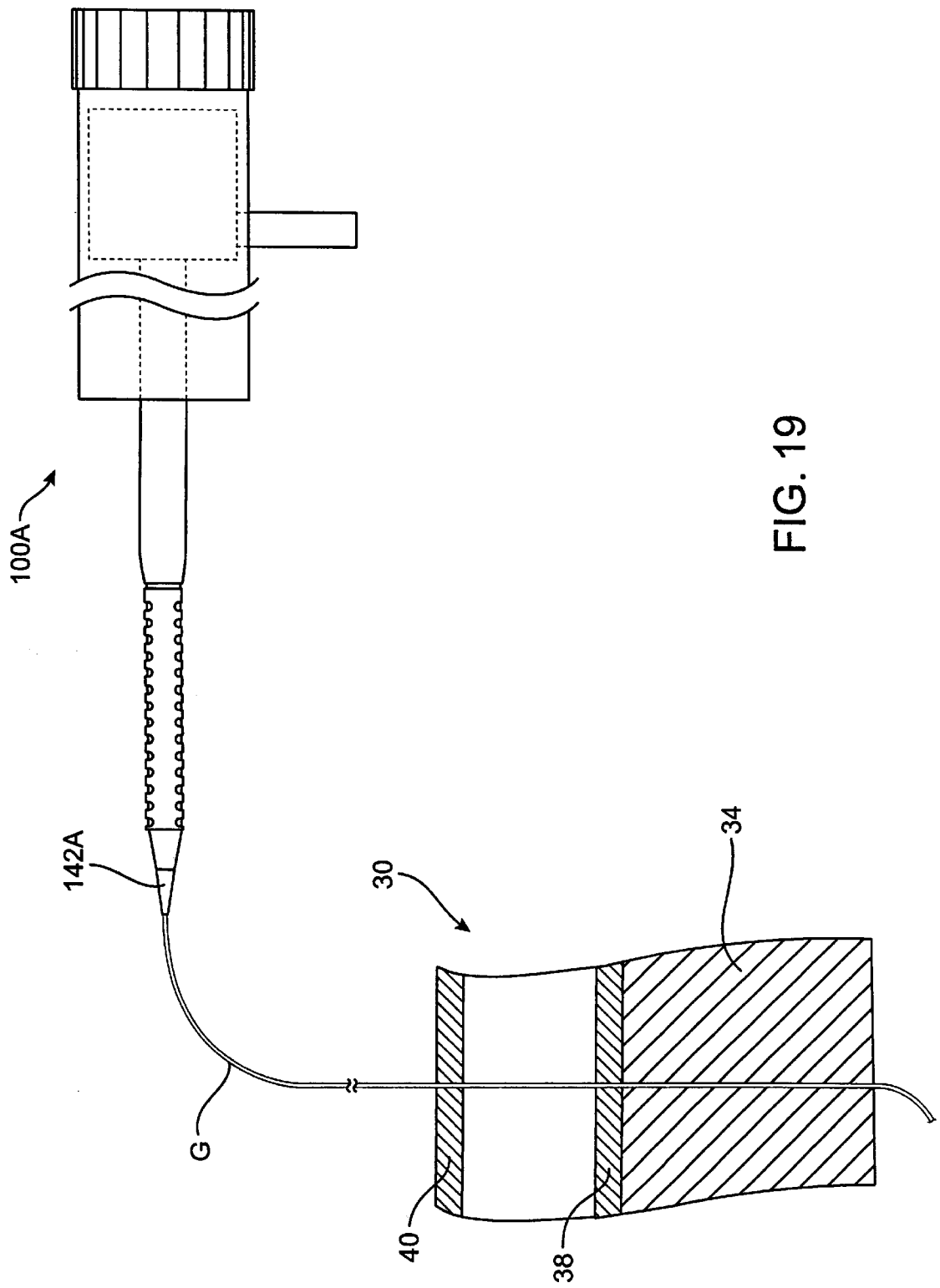
FIG. 19 is a perspective view illustrating the conduit placement device shown in FIGS. 3–6A being used with a guide member positioned through a coronary vessel and a heart wall.
Figure 20:
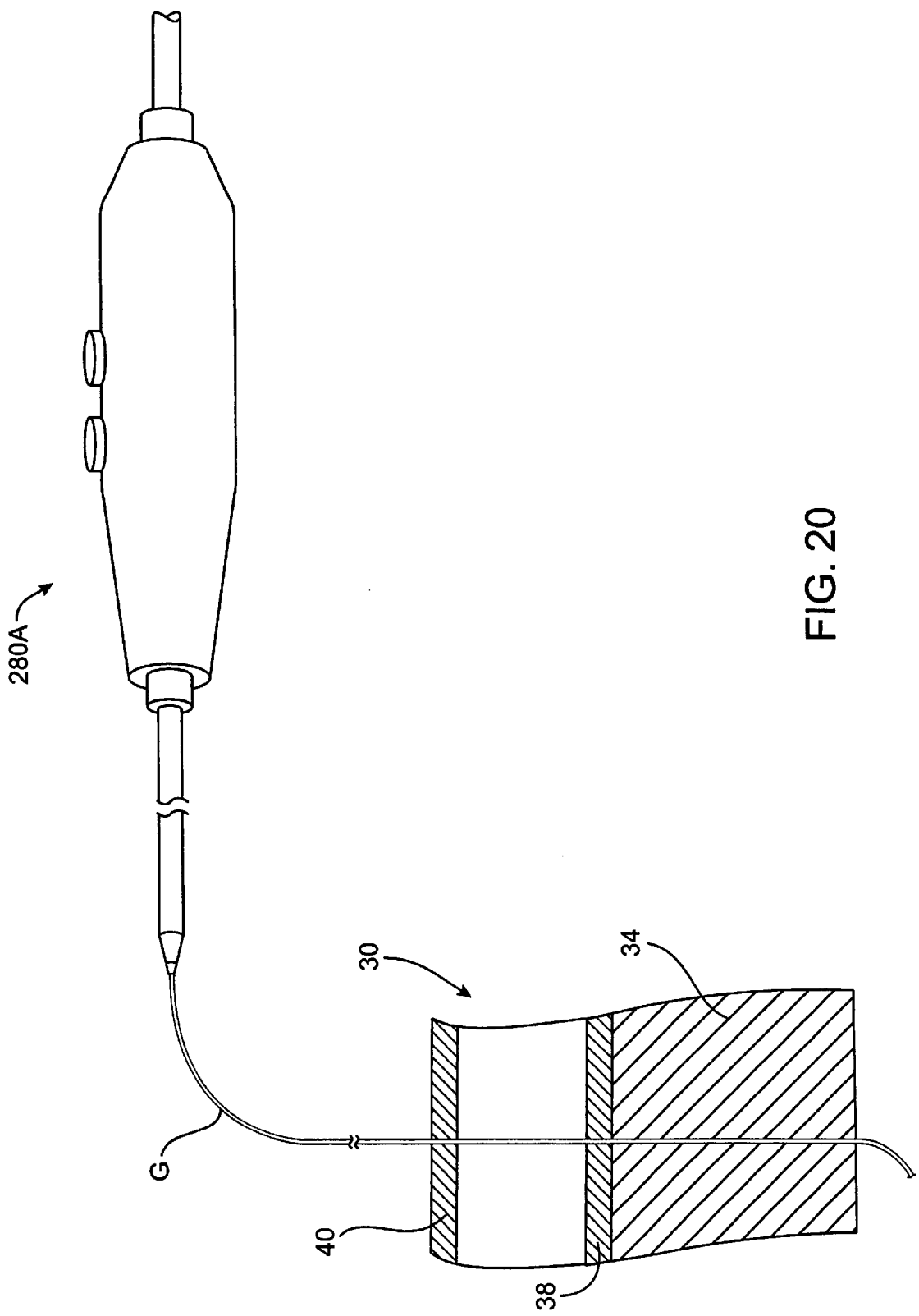
FIG. 20 is a perspective view illustrating the tissue removal device shown in FIGS. 17–18C being used with a guide member positioned through a coronary vessel and a heart wall.

FIGS. 19 and 20 show alternative embodiments of the invention wherein a guide member is used to introduce a conduit delivery device and a tissue removal device, respectively. FIG. 19 shows a guide member G, which may be in the form of a guide wire, and a conduit delivery device 100A having a similar construction as the device 100 illustrated in FIGS. 3–6C. The guide member G passes through the coronary vessel (LAD 30) and the heart wall 34. The device 100A has a central bore, for example, through the dilator 142A, which allows the device to be passed over the guide member G. Thus, this embodiment utilizes a guide member to aid in passing the delivery device through the coronary vessel and the heart wall into the heart chamber, the device being then being used to place a conduit in the heart wall as described above.

Similarly, FIG. 20 shows another alternative embodiment of the invention including a guide member G which may be in the form of a guide wire, and a tissue removal device 280A constructed in a similar manner as the device 280 illustrated in FIGS. 17–18C. As above, the guide member G passes through the coronary vessel and the heart wall and is used to place the device 280A in the heart wall. The tissue removal device 280A has a central bore that receives the guide member to place the device through the coronary vessel and the heart wall into the heart chamber. The device 280 is then used as described above to form a channel in the heart wall.

It will be understood that the embodiments shown in FIGS. 19–20 are only exemplary in that any medical device configured to carry out a medical procedure may be introduced using a guide member placed through the coronary vessel and the heart wall, the conduit delivery and tissue removal devices disclosed herein being exemplary. Further, it should be recognized that the guide member may be placed through the coronary vessel and the heart wall by any suitable method and system, and that the devices may be pushed over the guide member or secured thereto and pulled into the heart chamber. For example, the guide member may be placed and used as disclosed in co-pending, commonly owned application, U.S. application Ser. No. 09/170,793, filed on Oct. 13, 1998, and entitled "PLACING A GUIDE MEMBER INTO A HEART CHAMBER THROUGH A CORONARY VESSEL AND DELIVERING DEVICES FOR PLACING THE CORONARY VESSEL IN COMMUNICATION WITH THE HEART CHAMBER," the disclosure of which is incorporated herein by reference.

It should be noted that, as used herein, the term conduit refers to any structure that is capable of conveying fluid from one point to another, for example, a tubular element with two or more open ends. In view of the fact that various characteristics of the conduit, for example, size, shape and surface configuration, may vary depending on the application, it will be recognized that the conduits in the illustrated embodiments are merely exemplary. For instance, the conduit could be a rigid or flexible tubular element with solid or perforated walls, the conduit could be straight over its length with the ends aligned or the ends could be offset, the exterior surface of the conduit may be treated to enhance fixation of the conduit in the heart wall, and the conduit may or may not include a valve or other flow controlling mechanism.

It should also be noted that the various aspects of the invention incorporated in the illustrated embodiments may be used together or separately. For instance, a sheath and a positioning member constructed according to the invention can take different forms and may be used without each and with any type of conduit. Likewise, the methods disclosed herein may be modified without departing from the principles of the invention. For example, the methods may be carried out by combining particular steps or varying the sequence of steps.

It will be understood that the invention encompasses many variations of the preferred systems and methods described in detail herein. For example, the surgical approach depicted in FIG. 1 is but one exemplary manner of accessing the heart in order to utilize the systems, devices and methods of the invention. The approach illustrated in FIG. 1, which can be characterized as minimally invasive in that a thoracotomy is used as opposed to a median sternotomy, may be desirable in some applications. However, those skilled in the art will recognize that other approaches may be used to access the heart in order to practice the invention.

For example, an open surgical procedure including a median sternotomy may be used, or a minimally invasive procedure utilizing one or more relatively small access openings or ports may be used. Endoscopes or thoracoscopes may be used for visualization if the procedure is truly minimally invasive. Additionally, rather than forming one or more incisions in the patient's chest wall, an endovascular approach may be used to guide various inventive devices to the heart through the patient's vascular system to the heart, for example, by introducing the devices into a peripheral vessel such as the femoral artery. If a surgical approach is used, the device may penetrate the outer and inner walls of the coronary vessel and then the heart wall, or a cut-down can be formed in the outer wall and the device passed into the vessel lumen and through the inner wall and the heart wall.

Further, the exemplary embodiments are described primarily in connection with their use in a beating heart procedure. Nevertheless, it will be recognized that the systems, devices and methods of the invention may be used in stopped-heart procedures utilizing cardiopulmonary bypass (CPB), or procedures during which the heart is intermittently stopped and started. For example, a conduit or channel formed according to the invention may be used to deliver various pharmaceutical substances, such as angiogenic growth factors or other substances that aid in the perfusion of surrounding myocardial tissue. As a result, the detailed description of preferred embodiments set forth in the drawing Figures and accompanying disclosure should not be construed as limiting the applications for which the invention may find utility.

The preferred embodiments of the invention are described above in detail for the purpose of setting forth a complete disclosure and for sake of explanation and clarity. It will be readily understood that the scope of the invention defined by the appended claims will encompass numerous changes and modifications to the embodiments disclosed herein.

What is claimed is:

1. A method for placing a conduit in the wall of a patient's heart, the method comprising steps of:
   (a) providing a support member and a conduit;
   (b) passing the support member and the conduit through an exterior wall of a coronary vessel and through the wall of a patient's heart;
   (c) positioning the conduit within the wall of the heart; and
   (d) removing the support member from the wall of the heart.

2. The method of claim 1, wherein a sheath overlies the conduit, and further comprising the step of moving the sheath to expose the conduit once a shaft and conduit are positioned in the wall of the heart.

3. The method of claim 2, wherein the conduit is expandable and the support member is provided with an expandable member that supports and expands the conduit, and further comprising the step of expanding the conduit within the wall of the heart.

4. The method of claim 1, wherein step (b) is carried out by passing a sharpened end of the support member through the wall of the heart.

5. The method of claim 1, wherein step (b) is carried out by first forming an opening extending at least partially through the wall of the heart and then passing the support member through the opening.

6. The method of claim 5, wherein the coronary vessel is a coronary artery and the heart chamber is the left ventricle.

7. The method of claim 1, wherein the conduit is passed through a wall of a coronary vessel and through the wall of the heart into a heart chamber containing oxygenated blood, and the conduit is positioned so as to place the heart chamber in communication with the interior of the coronary vessel.

8. The method of claim 7, further comprising positioning a support mechanism within the heart chamber to support the heart wall during at least steps (b) and (c).

9. A method for placing a conduit in the wall of a patient's heart at a selected position with respect to the heart wall, the method comprising steps of:
   (a) providing a support member and a conduit, the support member having a positioning member disposed at a predetermined location with respect to the conduit;
   (b) passing the support member and the conduit through a wall of a coronary vessel and through the wall of a patient's heart;
   (c) locating the positioning member against tissue to place the conduit at a selected location within the wall of the heart; and
   (d) removing the support member and leaving the conduit in the wall of the heart.

10. The method of claim 9, wherein a sheath overlies the conduit, and further comprising the step of moving the sheath to expose the conduit once the shaft and conduit are positioned in the wall of the heart.

11. The method of claim 10, wherein the conduit is expandable and the support member is provided with an expandable member that supports and expands the conduit, and further comprising the step of expanding the conduit within the wall of the heart.

12. The method of claim 9, wherein step (b) is carried out by passing a sharpened end of the support member through the wall of the heart.

13. The method of claim 9, wherein step (b) is carried out by first forming an opening extending at least partially through the wall of the heart and then passing the support member through the opening.

14. The method of claim 9, wherein the conduit is passed through a wall of a coronary vessel and through the wall of the heart into a heart chamber containing oxygenated blood, and the conduit is positioned so as to place the heart chamber in communication with the interior of the coronary vessel.

15. The method of claim 14, wherein the coronary vessel is a coronary artery and the heart chamber is the left ventricle.

16. The method of claim 9, wherein a support mechanism contacts and supports the heart wall during at least steps (b) and (c).

* * * * *